United States Patent [19]

Uda et al.

[11] Patent Number: 5,147,783
[45] Date of Patent: Sep. 15, 1992

[54] METHODS TO SCREEN FOR OVARIAN CANCER AND MYOCARDIAL INFARCTION

[75] Inventors: Taizo Uda; Yukikatsu Itoh; Tetsuo Kawaguchi; Emi Hifumi, all of Ube; Naoyuki Taniguchi, Toyonaka; Keiichiro Suzuki, Takatsuki; Mutsuo Ishikawa, Asahikawa; Shirou Noji, Tokyo, all of Japan

[73] Assignee: Ube Industries, Ltd., Ube, Japan

[21] Appl. No.: 352,109

[22] Filed: May 15, 1989

[30] Foreign Application Priority Data

| May 27, 1988 | [JP] | Japan | 63-128165 |
| Jul. 15, 1988 | [JP] | Japan | 63-175129 |
| Mar. 3, 1989 | [JP] | Japan | 1-50005 |
| Mar. 7, 1989 | [JP] | Japan | 1-52780 |

[51] Int. Cl.$^5$ ............... G01N 33/543; G01N 33/574; G01N 33/573; G01N 33/577
[52] U.S. Cl. .................. 435/7.23; 435/7.4; 435/240.27; 436/518; 436/548; 436/813; 530/388.26
[58] Field of Search ............ 435/7.9, 7.92, 172.2, 435/290.27, 7.23; 436/548, 518, 813; 530/387

[56] References Cited

FOREIGN PATENT DOCUMENTS 58-086098 5/1983 Japan .

OTHER PUBLICATIONS

Kawaguchi et al. *J. Biol. Chem.* 264(10):5762, 1989.
Iizuka et al. *J. Natl. Cancer Inst* 72(5):1043, 1984.
Iizuka *Hokkaido J. Med. Sci.* 59(6):739, 1985.
Köhler et al. *Nature* 256:495, 1975.
Oberley et al. *Cancer Res.* 39:1141, 1979.
Kumari et al. *Indian J. Exp. Biol.* 25(6):419, 1987.

*Primary Examiner*—Esther L. Kepplinger
*Assistant Examiner*—Arti Shah
*Attorney, Agent, or Firm*—Frishauf, Holtz, Goodman & Woodward

[57] ABSTRACT

A monoclonal antibody against human manganese-superoxide dismutase characterized in that it is produced by a cell line which has been obtained by immunization of a mouse with human Mn-SOD and then fusion of lymphocytes obtained from the mouse with mouse myeloma cells, and has high specificity against human Mn-SOD; a method for producing a monoclonal antibody against human Mn-SOD having high specificity against human Mn-SOD, which comprises culturing the cell line obtained by immunization of a mouse with human Mn-SOD and then cell fusion of lymphocytes obtained from the mouse with mouse myeloma cells; a kit for assaying human Mn-SOD, comprising:

(a) a monoclonal antibody having very high specific immuno-reactivity against human Mn-SOD; and
(b) a reagent of a monoclonal antibody having very high specific immuno-reactivity against human Mn-SOD labelled with an enzyme (enzyme labelled antibody); a method for assaying human Mn-SOD use of the kit; a novel diagnostic method of human epithelial ovarian cancer, which comprises assaying the concentration of human Mn-SOD in a body fluid by use of the assay kit; and a novel diagnostic method of myocardial infarction, which comprises assaying the concentration of human Mn-SOD in a body fluid by use of the assay kit.

4 Claims, 16 Drawing Sheets

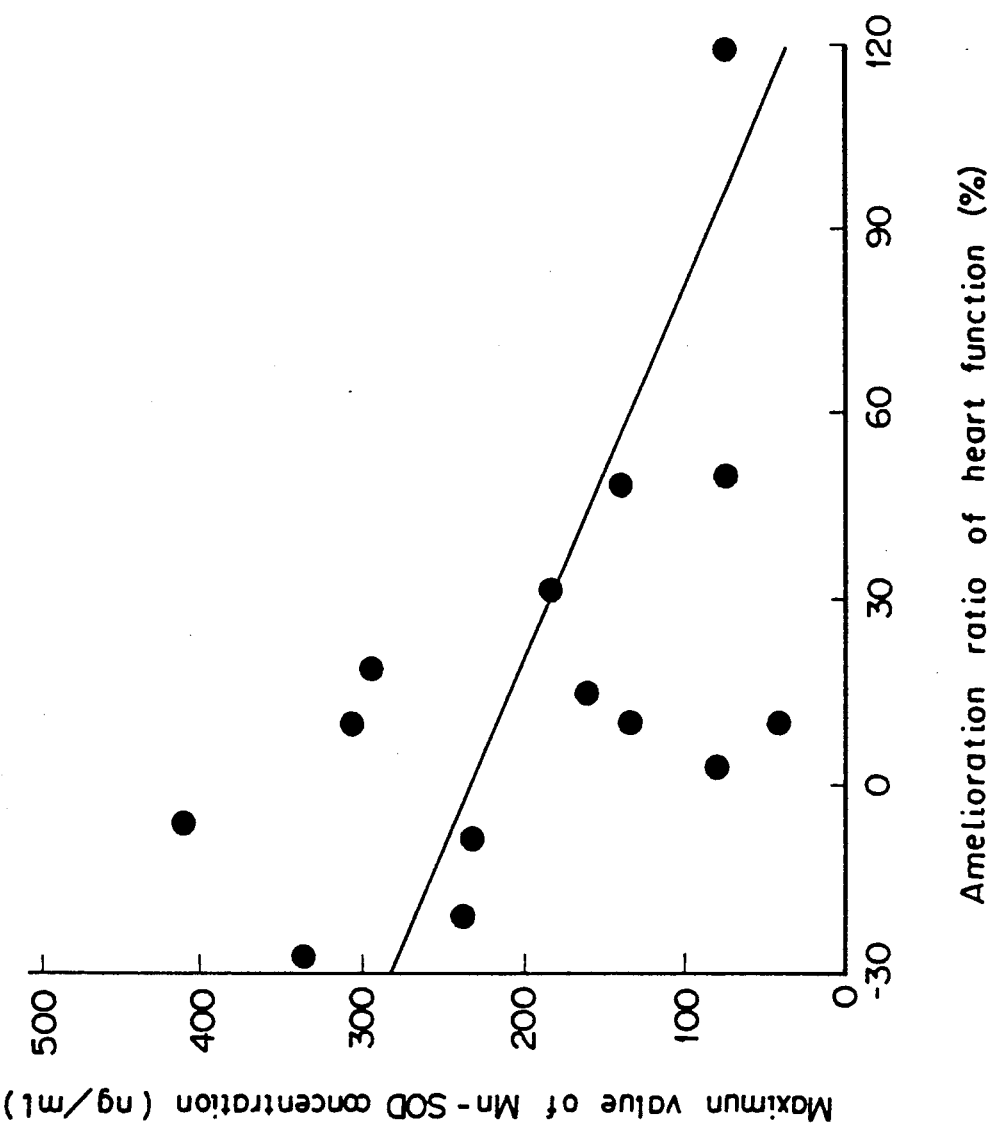

METHODS TO SCREEN FOR OVARIAN CANCER AND MYOCARDIAL INFARCTION

BACKGROUND OF THE INVENTION

This invention relates to a monoclonal antibody having high specificity against human manganese-superoxide dismutase (hereinafter abbreviated as human Mn-SOD), a method for producing the monoclonal antibody, an assay reagent or assay kit and assay method by use thereof, and a diagnostic method of human ovarian cancer and myocardial infarction by use thereof.

Human Mn-SOD is an enzyme (with a molecular weight of one domain being about 25,000, and comprising a dimer or tetramer thereof) existing in the matrix portion of mitochondrion, and catalyses the reaction of disproportionating superoxide anion radical ($O_2^-$) which is the main molecular species of active oxygen as shown below:

$$2\ O_2^- + 2\ H^+ \rightarrow H_2O_2 + O_2.$$

Whereas, female gynecological cancers include cervical cancer of the uterus, endometrial cancer of the uterus, ovarian cancer, choriocarcinoma, etc. Among them, generation of cervical cancer of the uterus has been constantly reduced year by year, and the choriocarcinoma can be now expected to have high therapeutical effect. However, endometrial cancer of the uterus and ovarian cancer have many problems in an early diagnostic method, therapeutical method, monitoring of prognosis, etc.

Among them, ovarian cancer is generated in all the classes of age from the classes of infant and young women to old women, and is increasing year by year, particularly at a greater ratio in women of fifties or older [Mori, Miyake: Japanese Journal of Cancer Research (Gan), vol. 79, No. 12, 1988]. Also, in therapy of a malignant group of ovarian cancers with extremely poor prognosis, it has been earnestly desired to establish an excellent early diagnosis method.

Accordingly, as the method for diagnosis of ovarian cancer up to date, there are examples in which α-fetoprotein, carcinoembryonic antigen, human chorionic gonadotropin or CA125 which is the cell surface sugar chain antigen of cultured cell line derived from ovarian cancer, etc. are used as the diagnosis marker for investigation (Masato Mochizuki: Rinsho Byori (Clinical Pathology), vol. 34, No. 11, 1986; Kazuo Omi et al: The 9th Clinical Chemical Test Technology Course Text, 1989). However, in the above method, in the case of α-fetoprotein, probably because it was developed as the diagnosis marker for hepatoma, the positive ratio for epithelial ovarian cancer is 0%; in the case of carcinoembryonic antigen, the positive ratio for epithelial ovarian cancer is 12%; and in the case of human chorionic gonadotropin, the positive ratio for epithelial ovarian cancer is 0%. On the other hand, in the case of CA125 which is the cell surface sugar chain antigen of cultured cell line derived from ovarian cancer, the positive ratio for epithelial ovarian cancer is high as 94%, but exhibits 21% for endometrial cancer of the uterus, and also 30% for endometriosis. Therefore, for diagnosis of epithelial ovarian cancer by use of these diagnosis markers, all of the methods involve problems in their positive ratios and/or specificities.

On the other hand, myocardial infarction is a disease causing ischemia, myocardiopathy, necrosis of myocardium by occlusion and stenosis through the coronary artery, and the acute stage lethality is still at a high value, thus posing a social problem also because of sudden sideration in the generation of people in their prime.

Accordingly, as a countermeasure for its therapy, it is necessary to know the site of myocardial infarction, the size, the course and the prognosis of the lesion by changes in a electrocardiogram, left ventriculography contrast, and fluctuation in serum enzyme.

Fluctuation in serum enzyme is the biochemical diagnostic method to know the fluctuation in deviated enzyme freed out because of myocardial necrosis, and as such method, there have been known the methods in which GOT (glutamic oxaloacetic transaminase), CPK (creatin phosphokinase), LDH (lactic dehydrogenase), etc. are used.

However, according to the biochemical diagnostic methods by use of these enzymes, the enzyme amount exhibits the maximum value within a short time from the onset of stroke of myocardial infarction in most cases, and since these peaks of enzyme coronary angioplasty (the catheter method) (Yoichi Shimizu et al; Nippon Rinsho (Japanese Clinic), vol. 45, 1987, extra No.), percutaneous transluminal coronary recanalization (Katsuo Uematsuse et al: Nippon Rinsho (Japanese Clinic), vol. 45, extra No., 1987), etc. which are the principal methods of myocardial infarction, it is difficult to diagnose accurately myocardial infarction, and also there is the problem that frequent blood sampling is required at the initial stage from a stroke patient because these enzymes have a short time for persistence of a high value of concentration in blood.

On the other hand, it has been considered that a high diagnostic significance exists in the assay of human Mn-SOD concentration in serum in liver disease by the investigations by use of a polyclonal antibody (Iyaku Journal (Journal of Pharmaceutical): Inagaki, Sawaki, 20, 1, 1984; The 5th Marker Research Society, Iizuka, Arai et al, 1985). Also, Taniguchi et al reported that human Mn-SOD concentration was high in lung cancer tissue by the immunological method by use of a polyclonal antibody prepared by immunization of goat (Journal of National Cancer Institute, 72, 5, 1984), and importance of an assay of human Mn-SOD concentration in serum is pointed out.

However, since polyclonal antibodies are used in an assay of human Mn-SOD concentration in serum in these various diseases, it is necessary to produce a monoclonal antibody and establish a method for production thereof in order to further enhance the specificity of the reaction for human Mn-SOD and also obtain constantly an antibody having a high specific reactivity of the same quality, but there has been yet recognized no report concerning a monoclonal antibody having a very high specific reactivity against human Mn-SOD.

A first object of the present invention is to provide a monoclonal antibody having a very high specific reactivity against human Mn-SOD in human serum, and a method for producing the monoclonal antibody.

A second object of the present invention is to provide an assay reagent or an assay kit and an assay method of human Mn-SOD by use of a monoclonal antibody having a very high specific immunoreactivity against human Mn-SOD.

A third object of the present invention is to provide a novel diagnostic method of human epithelial ovarian cancer such as epithelial carcinogenesis of the human ovary and monitoring of its prognosis by assaying the human Mn-SOD concentration in human body fluid by use of the assay reagent or the assay kit of human Mn-SOD comprising a monoclonal antibody as mentioned above.

A fourth object of the present invention is to provide a novel method of myocardial infarction such as sideration of myocardial infarction and monitoring of its prognosis by assaying the human Mn-SOD in human body fluid by use of the assay reagent or the assay kit of human Mn-SOD comprising a monoclonal antibody as mentioned above.

The present inventors have studied intensively in order to solve the above problems and consequently found that a monoclonal antibody exhibiting a very high specific reactivity against human Mn-SOD can be produced by culturing the cell line obtained by immunizing a mouse with human Mn-SOD followed by cell fusion; that human Mn-SOD can be assayed easily and at a high sensitivity by assaying human Mn-SOD by use of an assay reagent or an assay kit of human Mn-SOD by use of the above antibody; that diagnosis of ovarian cancer such as epithelial carcinogenesis of the human ovary and monitoring of its prognosis can be easily performed at a high positive ratio and specificity by assaying human Mn-SOD concentration in human body fluid by use of the assay reagent or the assay kit; and that the diagnosis method of myocardial infarction by use of the assay reagent or the assay kit of human Mn-SOD is not affected at all by reperfusion after therapy, and also requires no frequent blood sampling, and therefore diagnosis such as sideration of myocardial infarction and monitoring of its prognosis can be easily performed, to accomplish the present invention.

SUMMARY OF THE INVENTION

More specifically, the present invention, in a first aspect, provides a monoclonal antibody against human Mn-SOD, characterized in that it is produced by the cell line obtained by immunizing a mouse with human Mn-SOD and fusing the lymphocytes obtained from the mouse with mouse myeloma cells and has a high specificity against human Mn-SOD, and further a method for producing a monoclonal antibody against human Mn-SOD having a high specificity, which comprises culturing the cell line obtained by immunizing a mouse with human Mn-SOD and fusing the lymphocytes obtained from the mouse with mouse myeloma cells.

The present invention, in a second aspect, provides a reagent or a kit for assaying human Mn-SOD, comprising essentially:
(a) a monoclonal antibody having a very high specific immuno-reactivity against human Mn-SOD; and
(b) a reagent of a monoclonal antibody having a very high specific immuno-reactivity against human Mn-SOD labelled with an enzyme, and a method for assaying human Mn-SOD, which comprises immobilizing the monoclonal antibody as defined above on a carrier, and then carrying out the reaction of the immobilized monoclonal antibody, human Mn-SOD in a sample to be measured and the monoclonal antibody as defined above labelled with an enzyme, thereby preparing a complex comprising the monoclonal antibody immobilized on the carrier, human Mn-SOD and the monoclonal antibody labelled with the enzyme.

The present invention, in a third aspect, provides a novel diagnostic method of human epithelial ovarian cancer, which comprises assaying the concentration of human Mn-SOD in a body fluid by use of an assay reagent or an assay kit for human Mn-SOD comprising a monoclonal antibody having a very high specificity against human Mn-SOD.

The present invention, in a fourth aspect, provides a novel diagnosic method of myocardial infarction, which comprises assaying the concentration of human Mn-SOD in a body fluid by use of an assay reagent or an assay kit for human Mn-SOD comprising a monoclonal antibody having a very high specificity against human Mn-SOD.

BRIEF DESCRIPTION OF THE DRAWINGS

FIG. 16 shows the relationship between the maximum value of Mn-SOD concentration at a "diagnosis stage" in each serum of 14 cases of myocardial infarction patients and amelioration ratio of heart function.

DESCRIPTION OF THE PREFERRED EMBODIMENTS

Figure 1:
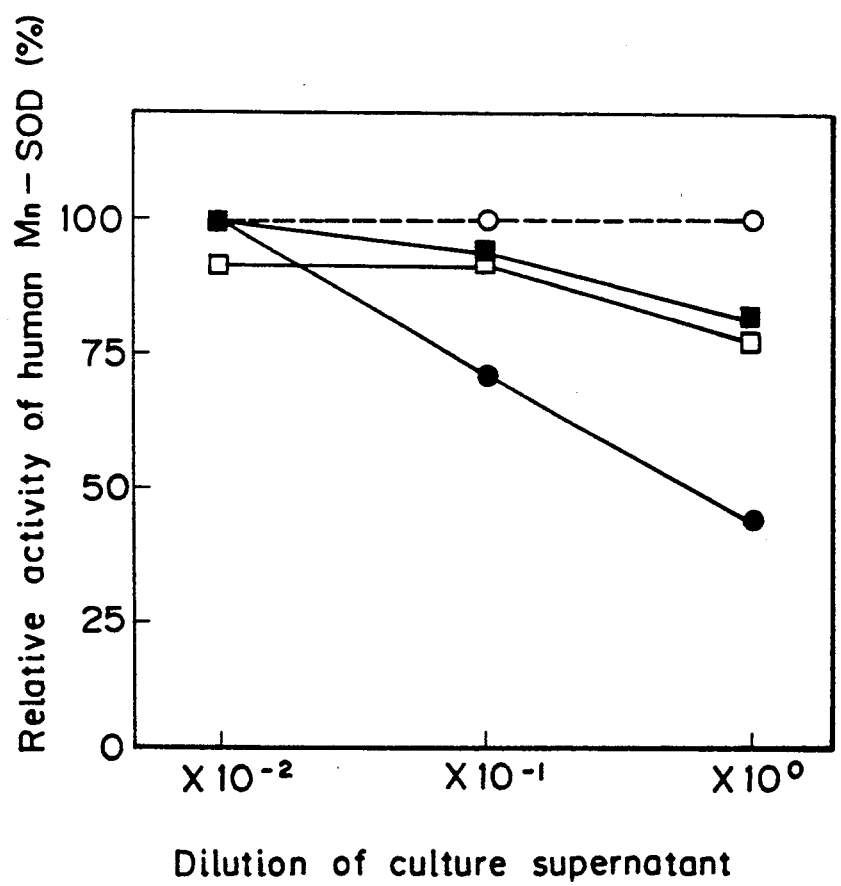
FIG. 1 shows relative activity of human Mn-SOD in the supernatant obtained by mixing human Mn-SOD with a culture supernatant containing NI8 (□), PE9 (■) or PG11 (●) (used with dilution to 1-fold, 10-fold or 100-fold), incubating the mixture at 37° C. for 30 minutes, then adding protein A agarose and further incubating the mixture at 37° C. for 10 minutes, followed by centrifugation. For a control, the culture supernatant of NS-1 cell line (○) was employed.

The monoclonal antibody of the present invention is produced by a cell line obtained by immunizing a mouse with human Mn-SOD and then effecting cell fusion, and has a very high specific reactivity against human Mn-SOD.

As the immunogen to be used for immunization of mouse in the present invention, any material capable of providing a monoclonal antibody having a very high specific reactivity against human Mn-SOD may be used without any particular limitation, but, for example, there can be employed monomers constituting human Mn-SOD, human Mn-SOD, and a synthesized peptide comprising a part of human Mn-SOD, etc. Preferably, human Mn-SOD may be employed.

The monoclonal antibody having a high specificity against human Mn-SOD has no reactivity against human Cu, Zn-superoxide dimustase (hereinafter abbreviated as human Cu, Zn-SOD), a human albumin, human globulins. The monoclonal antibody having such specificity can be obtained, for example, by culturing NI8 cell line (FERM-P No. 1606), PE9 cell line (FERM-P No. 1607), PG 11 cell line (FERM-P No. 1608) which are hybridoma cell lines obtained by cell fusion of lymphocytes obtained from a mouse immunized with human Mn-SOD with myeloma cells.

Preparation of such hybridoma can be carried out according to the method known in the art, for example, the method of Milstein and Khöler [Nature, 256, 495 (1976)]. Preferable preparation methods of such hybridoma cell line are outlined sequentially below.

PREPARATION OF A HYBRIDOMA CELL LINE PRODUCING A MONOCLONAL ANTIBODY

Preparation of Immunized Animal Lymphocytes

Immunization of a mouse can be performed by administering human Mn-SOD (10 to 400 μg) dissolved in PBS (phosphate buffered saline) to a mouse once or several times at intervals of several weeks.

The first immunization can be also performed without administration of an adjuvant (immune promoting substance including alum, dead tuberclosis bacterial cells, nucleic acid, etc.), but it is preferable to administer an emulsion prepared by use of an adjuvant.

Lymphocytes can be obtained from blood, a lymph node, a spleen, etc. several days after the final immunization after confirmation of sufficient antibody value of a mouse which is the immunized animal, but preferably from a spleen.

(ii) Preparation of Myeloma Cells

For cell fusion, myeloma cells such as MPC-11, P3-X63-Ag8-653 (653), P3-X63-Ag8-UI (P3Ul), P3-NS-1 (NS-1), SP2/0-Ag14 (SP2/0), etc. derived from mice, and 210. RC Y3. Agl. 2. 3. (Y3) derived from rat, etc. can be used, but it is preferable to use myeloma cells which do not produce antibodies extracellularly secreted such as 653, P3Ul, NS-1, SP2/0, etc.

(iii) Cell Fusion

Cell fusion can be effected by mixing well the lymphocytes of the animal immunized as described above and myeloma cells at a ratio of cells (3 to 20): 1 with the use of a cell suspension which brings about no trouble in cell fusion, for example, a solution of medium components for culturing lymphocytes generally employed (medium components such as MEM, DMEM, McCoy, RPMI1640, etc.), isotonic buffer, etc., and adding HVJ (Sendai virus) or PEG (polyethylene glycol) solution to the pellet (mass of cells) after centrifugation, but it is preferable to use a PEG solution, more preferable a PEG solution of 30 to 60% by weight with an average molecular weight of 1000 to 8000. At this time, for promoting cell fusion, it is also possible to add colchicine, dimethyl sulfoxide, poly-L-arginine, etc.

As the myeloma cells to be used for cell fusion, those derived from animals heterologous from the immunized mouse can be also used, but in view of the aspects of antibody yield and stability of the monoclonal antibody producing hybridoma cell line, myeloma cells homologous with the immunized animals may be preferred, more preferably of the same cell line.

(iv) Selection of a Hybridoma

Selection of a hybridoma can be done by culturing the cells after the operation of cell fusion in HAT medium (medium containing hypoxanthine, aminopterin, thymidine, fetal bovine serum; as the medium components, medium components for cultivation of lymphocytes generally employed can be used).

Hybridomas can be cultured by placing a suitable number of cells for screening of an antibody producing well into each well (culturing well) in the culturing plate, and at this time, it is also possible to use a substance for promoting growth of a hybridoma or cells which produce it (e.g. lymphocytes derived from a thymus, spleen, or a lymph node) as feeder cells, if desired.

The hybridoma selected by growth in HAT medium is cultured for several days in HT medium (medium containing hypoxanthine, thymidine, fetal bovine serum; as the medium components, medium components for cultivation of lymphocytes generally employed can be used) until the cell number reaches suitable one for screening of antibody producing well, and further cultured in a medium for cultivation of lymphocytes containing fetal bovine serum generally used.

(v) Selection of an Antibody Producing Hybridoma

Assay of whether the hybridoma obtained in the above (iv) has produced the desired antibody or not can be practiced by the ELISA (enzyme-linked immunosobent assay), the plaque formation method, the agglutination reaction method, RIA (radioimmunoassay), the indirect fluorescent antibody technique (IFA), etc., but when the number to be assayed is very many, it should be preferably conducted according to the ELISA.

The ELISA may be carried out as described below. Into each well (assaying well) of the ELISA plate having human Mn-SOD fixed thereon, the hybridoma culture supernatant is added and left to stand stationarily for a certain period of time. Then, an enzyme-labelled antibody capable of reacting with the antibody derived from animal bound to each of these washed assaying wells to be bound thereto is added to these assaying wells, followed by leaving to stand stationarily for a certain period of time (the enzyme to be used for labelling may include, for example, peroxidase, alkaline phosphatase, β-galactosidase, etc.; the antibody to be labelled is not limited, so long as it is capable of reacting with only the antibody derived from the animal bound to the assaying well, as exemplified by sera obtained from mouse, rat, rabbit, goat, etc., or monoclonal antibodies produced by hybridoma cell lines prepared by use of mouse cells, etc.). Next, these assaying wells are washed, and a substrate solution corresponding to the enzyme employed is added for an assay of enzyme activity. If enzyme activity is recognized, it can be understood that the hybridoma producing the desired antibody exists in the culturing well from which the culture supernatant is sampled.

Thus, hybridomas in which cell growth is recognized and the antibody is produced can be obtained.

(vi) Cloning of a Hybridoma

The hybridoma in the culturing well in which antibody production is recognized can be cloned according to the limited dilution, the single cell manipulation (the method in which one hybridoma is placed in one well under inverted microscope), the method in which colony is picked up by use of soft agar, the method by use of FACS (Fluorescent Activated Cell Sorter), etc. At this time, the antibody producing hybridoma found in (v) is cultured according either one of the above cloning methods, and by use of the supernatant in the culturing well in which its growth is recognized, the antibody producing well is screened according to the same ELISA as practiced in selection of the antibody producing hybridoma in (v).

Thus, a hybridoma cell line producing a monoclonal antibody having a high specificity against human Mn-SOD and high antibody titer can be selected.

Method for Preparation of Monoclonal Antibody

Production of a monoclonal antibody having a high specificity against human Mn-SOD and a high antibody titer can be practiced by culturing the hybridoma cell line obtained in the above (vi) in a flask or intraperitoneally in an animal.

Production of said monoclonal antibody by cultivation in a flask of the hybridoma cell line obtained in the above (vi) can be carried out by, for example, culturing it in a medium for cultivation of lymphocytes generally used containing 0 to 20% of fetal bovine serum, for example, a medium containing medium components such as MEM, DMEM, McCoy, RPMI 1640 until the cell concentration reaches the upper limit. At this time, said monoclonal antibody is contained in the culture supernatant obtained by the centrifugal operation.

On the other hand, production of the hybridoma cell line obtained in the above (vi) can be also performed in an animal heterologous from the animal from which the cell used for cell fusion is derived, but it is preferably to use a homologous animal, more preferably an animal of the same cell line.

Production of said monoclonal antibody having a high specificity against human Mn-SOD and also a high antibody titer according to such method can be carried out by administering intraperitoneally into an appropriate animal such as a mouse, rat, hamster, etc. a substance which lowers the immune ability of such animal, for example, a mineral oil such as pristane, administering several weeks later $10^6$ to $10^7$ cells of the hybridoma cell line obtained in the above (vi), and growing the cell line intraperitoneally to a high density for several weeks. At this time, said monoclonal antibody is contained in the ascites supernatant obtained by the centrifugal operation. Then the antibody concentration is 10 to 1000-fold of the antibody concentration in the culture supernatant obtained during culturing in a flask. Said monoclonal antibody obtained by culturing of the hybridoma cell line in a flask or intraperitoneally in an animal may be purified by practicing salting out, dialysis, ion exchange chromatography, affinity chromatography applied for usually employed purification methods of proteins, thereby to become a monoclonal antibody of high purity.

Said monoclonal antibody obtained as described above has a very high specific reactivity with human Mn-SOD.

Next, the assay reagent or assay kit and the assaying method of human Mn-SOD of the present invention are to be described.

The assay reagent or assay kit of human Mn-SOD to be used in the assay method of human Mn-SOD of the present invention comprises essentially a monoclonal antibody having a very high specific immunoreactivity against human Mn-SOD (hereinafter abbreviated as "antibody") and a reagent comprising a monoclonal antibody having a very high specific immunoreactivity against human Mn-SOD labelled with an enzyme (hereinafter abbreviated as "enzyme-labelled antibody"). For assaying human Mn-SOD, in addition to these reagents, a carrier, a washing solution, a blocking solution, human Mn-SOD solutions of known concentrations for preparation of a calibration curve of human Mn-SOD (hereinafter abbreviated as "standard human Mn-SOD solution"), a substrate solution corresponding to the enzyme of the "enzyme-labelled antibody" (hereinafter abbreviated as a "substrate solution") are also required, and these may be previously assembled in the assay kit or prepared before assay. When the carrier is assembled previously in the assay kit of human Mn-SOD, the "antibody" can be also previously immobilized on the carrier. The "antibody" in the assay kit of human Mn-SOD of the present invention is not particularly limited, provided that it is a monoclonal antibody having a very high specificity against human Mn-SOD, and can include those produced by the above PG11 cell line (FERM-P No.1608) which is a hybridoma cell line, etc. As such "antibody", it is preferable to use one which is purified to high purity according to salting out by use of ammonium sulfate and ion exchange chromatography. If necessary, into the "antibody", a preservative for protein such as sodium azide, sodium ethylmercurithiosalcylate, etc. can be also added in a necessary amount.

In preparation of the "enzyme-labelled antibody" in the assay kit of human Mn-SOD of the present invention, as the enzyme labelling the "antibody", there can be included at least one kind of enzyme selected from oxidreductase, such as peroxidase, catalase, glucose oxidase, lactate oxidase, alcohol oxidase, monoamineoxidase, β-galactosidase, etc., and phosphate hydrolase such as alkaline phosphatase, etc.

The "antibody" labelled with the above enzyme is not particularly limited provided that it is a monoclonal antibody having a very high specificity against human Mn-SOD, and can include those produced by PGII cell line (FERM-P No.1608) which is a hybridoma cell line. As such "antibody", it is preferable to use one purified to high purity by salting out by use of ammonium sulfate and ion exchange chromatography.

Preparation of the "enzyme-labelled antibody" can be carried out by binding at least one "antibody" as described above with at least one enzyme as described above according to the one step method by use of glutaraldehyde [Immunochemistry, 6, 43 (1969)] or the two-step method [Immunochemistry, 8,1175 (1971)], the periodic acid oxidation method [Method in Enzymology, 37, 133 (1975)] or the maleimide method [Journal of the Biochemistry, 78, 235], but preferably according to the latter two methods.

This can be also used as such as "enzyme-labelled antibody", but for further enhancing assaying sensitivity of human Mn-SOD, it is preferable to use a product obtained by purifying this by gel filtration by use of Sephadex, Sephacryl, etc. as "enzyme-labelled antibody".

The "enzyme-labelled antibody" fraction obtained by such gel filtration can be also used as such (if the protein concentration is low, it is concentrated to a desired concentration, or if the protein concentration is high, it is diluted to a desired concentration), but it is preferable to dialyze it with a buffer adjusted to a pH around neutral (e.g. phosphate buffer or Tris-hydrochloride buffer), etc., store the dialysate after lyophilization or a sterilizing filter and reconstitute it, if desired, into "enzyme-labelled antibody" solution with a protein concentration of 0.01 to 100 μg/ml, preferably 0.1 to 10 μg/ml before use.

Also, if desired, into the "enzyme-labelled antibody", a preservative for protein such as sodium azide, sodium ethylmercurithiosalcylate, etc. can be also added in a necessary amount to the extent which has no trouble in assay of the enzyme activity.

A known amount of human Mn-SOD to be used for preparation of the calibration curve of human Mn-SOD of the present invention ("standard human Mn-SOD solution") can be obtained by purification by such method as heat treatment, ammonium sulfate fractionation, ion exchange chromatography, gel filtration, isoelectric point chromatography, etc. according to Journal of National Cancer Institute, 72, 5, (1984).

The carrier to be used in assay of human Mn-SOD of the present invention is required as the carrier for immobilizing the "antibody" in the assay kit of human Mn-SOD.

The shape of the carrier which can be used for immobilized human Mn-SOD in the present invention may include, for example, plate, tube, beads, membrane, etc. for immunoassay, and its material may include, for example, polyethylene, polystyrene, polypropylene, nitrocellulose, glass, etc.

The washing solution to be used in assay of human Mn-SOD in the present invention is required for removing materials not immobilized on the carrier by washing after having a predetermined amount of the "antibody" immobilized on the carrier, or for removing the unreacted substance after having human Mn-SOD in an assay sample reacted with the "antibody" immobilized on the carrier.

Examples of washing solution used for such purpose may include water, buffers adjusted to the pH during the reaction (buffers such as phosphate buffer, Tris-hydrochloride buffer, etc., the above-mentioned buffers containing 0 to 3 vol% of a surfactant such as Tween 20, Tween 60, etc.), but it is preferable to use a buffer adjusted to the pH during the reaction containing 0.02 to 0.8 vol% of the above surfactant.

The blocking solution to be used in the assay of human Mn-SOD in the present invention is required to prevent "enzyme-labelled antibody" or human Mn-SOD in the sample to be assayed from binding non-specifically onto the carrier surface, and can be also used as the solvent to be used when preparing a diluted solution of the sample to be assayed.

The blocking solution to be used for such purpose can be prepared by dissolving a high molecular weight protein such as bovine serum albumin (BSA), ovalbumin (OVA), keyhole limpet hemocyanin (KLH), γ-globulin, serum of various animals, etc. in the washing solution adjusted to the pH during the reaction as described above, and the concentration of these high molecular weight proteins may be 0.1 to 10 wt/vol%, preferably 0.1 to 2 wt/vol%. When it is prepared by use of serum of various animals, the concentration of serum may be made 1 to 50 vol/vol%, preferably 10 to 20 vol/vol% by use of the washing solution as described above.

Also, if desired, into the blocking solution, a preservative for protein such as sodium azide, sodium ethylmercury thiosalicylate, etc. can be added in a necessary amount.

As the assay sample to be used in the assay of human Mn-SOD in the present invention, human body fluids such as human urine, blood, serum, etc. as such or these assay samples diluted appropriately to the range in which human Mn-SOD can be assayed with the above washing solution can be used.

As the substrate solution for enzyme to be used in the assay of human Mn-SOD in the present invention ("substrate solution"), when the substrate with which the enzyme used in labelling of the antibody in an "enzyme-labelled antibody" reacts is $H_2O_2$, a buffer containing a substance which indicates a color with the substance formed by the enzymatic reaction such as o-phenylenediamine, 2,2'-aminobis(3-ethylbenzothiazoline-6-sulfonic acid (ABTS), etc. can be used when the substrate is paranitrophenyl phosphate, a buffer containing a substrate such as diethanolamine, etc. can be used.

As described above, by preparing a carrier, a washing solution, a blocking solution, a "standard human Mn-SOD solution", a "substrate solution", and by using an "antibody", an "enzyme-labelled antibody" which constitute the assay kit of human Mn-SOD, human Mn-SOD in a sample to be assayed can be assayed via the respective operational steps of each assay according to the stepwise reaction method or the mixed solution reaction method as described below.

(1) Step of Immobilizing Predetermined Amount of an "Antibody" on a Carrier

A predetermined volume of an "antibody" solution is contacted with a carrier for a certain period of time. The temperature during contact is not particularly limited, provided that the "antibody solution" is not freezed or boiled, but may be preferably 2° to 40 ° C.

(2) Step of Removing "Antibody" Not Immobilized on the Carrier

After the "antibody" solution is contacted with the carrier for a certain period of time, the "antibody" solution is removed, and further the "antibody" remaining without being immobilized on the carrier is removed by washing several times with a washing solution.

(3) Step of Preventing an Assay Sample and an "Enzyme-Labelled Antibody" From Non-Specific Binding Onto Carrier Surface Having No "Antibody" Immobilized Thereon A predetermined volume of a blocking solution is contacted with the carrier having the "antibody" in the above (2) for a certain period of time. The temperature during contact is not particularly limited, provided that the blocking solution is not freezed or boiled, but may be preferably 2° to 40 ° C.

(4) Step of Reacting "Antibody" Immobilized on Carrier, Human Mn-SOD and an "Enzyme-Labelled Antibody" to Obtain a Complex Comprising an "Antibody" Immobilized on a Carrier, Human Mn-SOD and an "Enzyme-Labelled Antibody" (Hereinafter Abbreviated as "Complex")

As the method for obtaining a "complex" by the reaction of the "antibody" immobilized on the carrier in the above (3), human Mn-SOD in the assay sample and the "enzyme-labelled antibody", there may be included the stepwise reaction method in which the "antibody" is reacted with the assay sample and then the "enzyme-labelled antibody" is reacted with the reaction product, or the mixed solution reaction method in which a mixed solution comprising the assay sample and the "enzyme-labelled antibody" is prepared, and the mixed solution is reacted with the "antibody".

In the stepwise reaction method, the "antibody" immobilized on the carrier in the above (3) is contacted with a predetermined amount of the assay sample to carry out the reaction for a certain period of time, and after removal of the unreacted mixture, the assay sample remaining without being immobilized through the "antibody" on the carrier is removed by washing several times with a washing solution, and subsequently a predetermined volume of "enzyme-labelled antibody" is contacted with human Mn-SOD immobilized through the "antibody" on the carrier to carry out the reaction for a certain period of time, whereby a "complex" can be obtained.

In the mixed solution reaction method, a mixed solution comprising the assay sample and the "enzyme-labelled antibody" is prepared, and by carrying out the reaction between a predetermined amount of the mixed solution and the "antibody" immobilized on the carrier in the above (3), "complex" can be obtained. When the mixed solution is prepared, it is preferable to make the reaction between the assay sample and the "enzyme-labelled antibody" under the inhibited state by way of, for example, ice-cooling, etc.

(5) Step of Removing Unreacted Mixture After Reaction of "Antibody" Immobilized on Carrier, Human Mn-SOD and "Enzyme-Labelled Antibody"

The unreacted mixture in the above (4) is removed by washing several times with a washing solution.

(6) Reaction of "Enzyme-Labelled Antibody Immobilized on the Carrier as "Complex" with "Substrate Solution"

As the "substrate solution" used here, one containing a substrate corresponding to the enzyme used in labelling of the antibody in the "enzyme-labelled antibody" and a substance which indicates a color through occurrence of the enzymatic reaction may be used.

A predetermined volume of the "substrate solution" is allowed to react with the "enzyme-labelled antibody" immobilized on the carrier as a "complex" for a certain period of time, but preferably the enzymatic reaction may be stopped by use of an acid such as $H_2SO_4$, etc., a base such as NaOH, etc. or an enzyme inhibitor. The reaction temperature may be within the optimum temperature range of the enzyme to be used at that time without any particular problem, but preferably 20° to 35 ° C.

(7) Step of Measuring Absorbance of Reaction Mixture After Enzymatic Reaction

The absorbance of the reaction mixture is measured at the wavelength when the color indication of the reaction mixture after the above enzymatic reaction exhibits the maximum absorbance.

As described above, from the results obtained by use of "standard human Mn-SOD solution" in place of the assay sample, the calibration curve is prepared, from which human Mn-SOD quantity in the assay sample can be assayed rapidly and at high sensitivity.

In the following, the novel diagnostic method of the present invention is to be described.

The novel diagnostic method of human epithelial ovarian cancer of the present invention exhibits a positive ratio of about 50% in human epithelial ovarian cancer, of about 30% in hapatoma, of about 15% in cervical cancer of the uterus, of about 7% in endometrical cancer of the uterus, of 0% in nonepithelical ovarian cancer and melanoma.

In the novel diagnostic method of human epithelial ovarian cancer of the present invention, an assay reagent or an assay kit of human Mn-SOD comprising a monoclonal antibody having immunoreactivity with a very high specificity against human Mn-SOD as described above and an assay method are used.

More specifically, according to the novel diagnostic method of human epithelial ovarian cancer of the present invention, in the case where the human Mn-SOD concentration exhibits a high value of 130 ng/ml (average value of healthy women + 2-fold of standard deviation value) or higher when the human Mn-SOD quantity is assayed as described above by use of a human body fluid as the assay sample, it can be diagnosed that the woman is highly probably afflicted with epithelial ovarian cancer, and also after assaying its concentration after the operation, it can be monitored whether the course of prognosis is under the state of either a regressed stage, a stabilized stage or a progressed stage.

In the novel diagnostic method of myocardial infarction, an assay reagent or assay kit of human Mn-SOD comprising a monoclonal antibody having immunoreactivity with a very high specificity against human Mn-SOD as described above and an assay method also as described above are used.

The novel diagnostic method of myocardial infarction of the present invention is not affected by reperfusion after therapy of myocardial infarction, and requires no frequent sampling of a body fluid, because the Mn-SOD concentration in human body fluid which is the biological index is persistent at a high value state of 150 ng/ml or higher during the period of about 110±10 hours after a stroke (the period in which such high value state is exhibited is hereinafter called "diagnosis stage"), and also body fluid can be sampled in "diagnosis stage" even after elapse of 2 days or longer after stroke.

The present invention is described in more detail by referring to Reference examples and Examples. These Examples are set forth only for illustrative purpose, and do not limit the present invention at all.

EXAMPLE 1

Preparation of Hybridoma Cell Line Producing a Monoclonal Antibody Against Human Mn-SOD (a) Immunization of a mouse and preparation of spleen lymphocytes:

An emulsion (0.5 ml) obtained by mixing thoroughly 1 ml of PBS (phosphate buffered saline, pH 7.4) containing 80 μg of human Mn-SOD dissolved therein and 1 ml of Freund's complete adjuvant was administered intraperitoneally into a BALB/c mouse (female, 8 weeks old).

Two weeks after the initial immunization, an emulsion (0.5 ml) prepared in the same manner as described above except for using Freund's incomplete adjuvant in place of Freund's complete adjuvant was administered intraperitoneally into the above mouse.

Further, two weeks later, as the final immunization, 0.2 ml of PBS containing 20 μg of the above human Mn-SOD dissolved therein was administered intravenously via the tail vein of the above mouse.

From the mouse thus immunized, on the 4th day from the final immunization, the spleen was enucleated, washed under ice-cooling in a petri dish containing 10 ml of RPMI1640 solution (medium powder for lymphocyte cultivation dissolved in distilled water), transferred into RPMI1640 solution newly prepared, divided into 4 equal portions with scissors and loosened with forceps.

The floated lymphocytes thus obtained were suspended in RPMI1640 solution, centrifuged (rotational number: 1000 rpm, time: 5 minutes), resuspended in RPMI1640 solution to provide mouse spleen lymphocytes to be used for cell fusion.

(b) Cell fusion $1.82 \times 10^7$ Mouse myeloma cells resistant to 8-azaguanine (NS-1) in the logarithmic growth phase and $1.39 \times 10^8$ mouse spleen lymphocytes as described above were placed in a conical centrifugal tube made of a plastic of 50 ml volume, mixed and then the supernatant was centrifuged (rotational number: 1500 rpm, time: 5 minutes), followed by loosening of the pellet by patting the same centrifugal tube.

While the pellet was shaken vigorously, 1 ml of 50% PEG 4000 solution (37° C.) was placed therein over one minute, followed further by vigorous shaking for 1 minute.

While the same centrifugal tube was gently shaken, 10 ml of RPMI1640 solution (37° C.) was added gradually over 3 minutes, and further 40 ml of RPMI1640 solution (37° C.) was added and the mixture was left to stand stationarily at room temperature for 20 minutes. Then, centrifugation was conducted at room temperature (rotational number: 1000 rpm, time: 5 minutes) to remove the supernatant by aspiration.

The same centrifugal tube was patted to loosen the pellet, which was suspended in 75 ml of HAT medium (RPMI1640 medium containing $1 \times 10^{-4}$M hypoxanthine, $4 \times 10^{-7}$M aminopterin, $1.6 \times 10^{-5}$M thymidine and 20% fetal bovine serum, maintained at 37° C.), and the suspension was added each in 100 μl into each culturing well of 7 culturing plates of 96-well, and cultivation was carried out by use of a $CO_2$ incubator (5% $CO_2$, 95% air, 37° C., humidity 100%).

On the 4th day and the 6th day after cell fusion, each 50 μl of the above HAT medium was added, and thereafter the mixture was exchanged with equal amount of 50 μl of HT medium (RPMI1640 medium containing $1 \times 10^{-4}$M hypoxanthine, $1.6 \times 10^{-5}$M thymidine and 20% fetal bovine serum, maintained at 37° C.) every 2 days.

(c) Selection of a hybridoma

Over 1 to 3 weeks from the initiation of culturing as described above (b), whether the antibody against human Mn-SOD was contained or not in the culture supernatant of each well in the culturing plate in which cell growth was recognized was investigated according to the ELISA as shown below.

First, into each assay well of a 96-well flat-bottomed ELISA plate, each 50 μl of a polyclonal antibody solution against human Mn-SOD (produced from goat, 100 μg/ml, dissolved in 0.05M carbonate buffer of pH 9.8) was added, and the mixture was left to stand stationarily at room temperature for 2 hours.

Subsequently, each assay well on the ELISA plate was washed twice with a washing solution (PBS containing 0.05% Tween 20), then each 100 μl of 0.1% OVA (ovalubmin) solution (dissolved in PBS) was added into each assay well, and the mixture was left to stand stationarily at room temperature for 30 minutes. Then, the mixture was washed twice with a washing solution, and each 50 μl of human Mn-SOD solution (1 μg/ml) was added into each well, followed by leaving to stand stationarily at 4° C. overnight. Each assay well was washed twice with the same washing solution, and then each 50 μl of the culture supernatant in each culturing well of the above culturing plate was added into each of these assay wells, followed by leaving to stand stationarily at 37° C. for one hour (for a negative Control, the supernatant obtained by culturing similarly mouse myeloma cells was used, while for a positive Control, the mouse serum used for cell fusion in the present invention diluted to 10-fold with the washing solution was used). Next, each assay well of the ELISA plate was washed 3 times with the washing solution, and each 50 μl of a horseradish peroxidase conjugated anti mouse IgG and IgM antibody solution was added into each assay well, followed by leaving to stand stationarily at room temperature for one hour. After each assay well of the ELISA plate was washed 4 times with the washing solution, each 100 μl of a substrate solution (prepared by dissolving 20 mg of o-phenylenediamine, 10 μl of 35% $H_2O_2$ in 50 ml of 0.1M citrate buffer of pH 5.0) was added into each assay well, and after the reaction at room temperature for 30 minutes under the state shielded from light, each 50 μl of 2N sulfuric acid was added into each assay well to stop the enzymatic reaction, followed by measurement of the absorbance of each well at 490 nm by use of an absorbance measuring device for microplate.

As the result of such investigation, in 8 wells among 678 culturing wells in the culturing plate, production of the antibody to human Mn-SOD was recognized.

(d) Cloning of a hybridoma

By use of RPMI1640 medium containing 20% fetal bovine serum, for one culturing well of the 8 culturing wells in which antibody production was recognized in the step (c) as described above, a hybridoma was cloned according to the limited dilution.

For cultivation, a 96-well culturing plate was used, and by use of thymus cell suspension of BALB/c mouse ($10^7$ cells/ml) as the feeder cell, cultivation was immobilized out at (0.1–5 hybridoma)/(100 μl thymus cell suspension)/well.

In cloning of the above one culturing well, the supernatant of the culturing well in which a single colony was observed from about the 10th day was collected and subjected to screening of antibody-producing well by the ELISA by use of human Mn-SOD (the same method as in the step (c) as described above). For the supernatants, in which antibody production against human Mn-SOD was recognized, further the reactivities with human globulin, human albumin and human Cu, Zn-SOD were examined according to the ELISA (the same method as in the step (c) as described above). Thus, each at least one hybridoma cell line having produced the antibody exhibiting reactivity against human Mn-SOD was obtained in each cloning, and these were recloned.

The cell line thus obtained is designated as NI8 cell line (FERM-BP No. 1606 deposited on Dec. 10, 1987 with the Fermentation Research Institute) and the monoclonal antibody produced by this cell line as NI8.

The class and the subclass of the monoclonal antibody contained in the culture supernatant of NI8 cell line were determined in the following assay test I, the reactivity of human Mn-SOD with the monoclonal antibody was identified in the assay test II, and reactivities with various proteins were examined in the assay test III.

ASSAY TEST I

Determination of Class and Subclass of Monoclonal Antibody Against Human Mn-SOD

Determination of the class and the subclass of the immunoglobulin produced by the NI8 cell line was conducted according to the Ouchterlony test by use of antibody solutions specific for respective classes and subclasses of mouse antibody (antibodies against $IgG_1$, $IgG_2a$, $IgG_2b$, $IgG_3$, IgM, IgA).

As the result, the monoclonal antibody produced by the NI8 cell line (NI8) was found to be an antibody belonging to the IgM Class.

ASSAY TEST II

Identification of Reactivity of Human Mn-SOD With Monoclonal Antibody

An amount 30 μl of human Mn-SOD (10 μg/ml) was mixed with 50 ml of a culture supernatant containing 50 ml NI8 (used with dilution of 1-fold, 10-fold or 100-fold) to carry out the reaction at 37° C. for 30 minutes, then 10 μl of a protein A agarose solution (amount of bound protein A: 1 to 2 mg/ml agarose gel) to carry out further the reaction at 37° C. for 10 minutes, followed by centrifugation (rotational number: 10,000 rpm, time: 5 minutes) and an assay of human Mn-SOD activity of the supernatant (for negative Control, the supernatant of myeloma was employed).

As the result, human Mn-SOD activity was found to be lowered (shown in FIG. 1).

ASSAY TEST III

Examination of Reactivities of Monoclonal Antibody Against Human Mn-SOD With Various Proteins For reaction specificity of NI8, reactivities with various proteins such as human albumin, human globlins, human Cu, Zn-SOD, human Mn-SOD were examined according to the Western blotting method. As the result, NI8 was recognized to have high specific reactivity against human Mn-SOD, with no reactivity with other proteins being recognized.

EXAMPLE 2

Preparation of a Hybridoma Cell Line Producing Monoclonal Antibody Against Human Mn-SOD (a) Immunization of a mouse and preparation of spleen lymphocytes Similarly as in Example 1, immunization and preparation of spleen lymphocytes were conducted.

(b) Cell fusion

Of the operations as described in Example 1, the same operations were repeated except for using $1.7 \times 10^7$ mouse myeloma cells (P3U1) resistant to 8-azaguanine in the logarithmic growth phase and $8.5 \times 10^7$ mouse spleen cells prepared as described above.

(c) Selection of a hybridoma

The same operations as described in Example 1 were repeated.

As the result of such investigations, production of antibody against human Mn-SOD was recognized in 20 wells among 678 culturing wells in the culturing plate.

(d) Cloning of a hybridoma

By use of RPMI1640 medium containing 20% fetal bovine serum, for one of the 20 culturing wells in which antibody production was recognized shown in the step (c) as described above, the same operations as in Example 1 were conducted to effect cloning of hybridoma.

The cell line thus obtained is designated as PE9 cell line (FER-BP) No. 1607 deposited on Dec. 10, 1987 with the Fermentation Research Institute) and the monoclonal antibody produced by this cell line as PE9.

Various properties of the monoclonal antibody contained in the culture supernatant of the PE9 cell line were investigated by carrying out the same operations as in Example 1. As the result, the class and subclass of PE9 were found to belong to the IgM Class. The human Mn-SOD activity of the supernatant obtained by the reaction of PE9 with protein A agarose solution was lowered (as shown in FIG. 1). PE9 was recognized to have high specific reactivity against human Mn-SOD, and no reactivity with other proteins.

EXAMPLE 3

Preparation of Hybridoma Cell Line Producing Monoclonal Antibody Against Human Mn-SOD (a) Immunization of a mouse and preparation of spleen lymphocytes Similarly as in Example 1, immunization and preparation of spleen lymphocytes were conducted.

(b) Cell fusion

Of the operations as described in Example 1, the same operations were repeated except for using $1.4 \times 10^7$ mouse myeloma cells (P3U1) resistant to 8-azaguanine in the logarithmic growth phase and $5.3 \times 10^7$ mouse spleen cells prepared as described above.

(c) Selection of a hybridoma

The same operations as described in Example 1 were repeated.

As the result of such investigations, production of antibody against human Mn-SOD was recognized in 15 wells among 678 culturing wells in the culturing plate.

(d) Cloning of a hybridoma

By use of RPMI1640 medium containing 20% fetal bovine serum, for one of the 15 culturing wells in which antibody production was recognized shown in the step (c) as described above, the same operations as in Example 1 were conducted to effect cloning of a hybridoma.

The cell line thus obtained is designated as PG11 cell line (FERM-BP No. 1608 deposited on Dec. 10, 1987 with the Fermentation Research Institute and the monoclonal antibody produced by this cell line as PG11.

Various properties of the monoclonal antibody contained in the culture supernatant of the PG11 cell line were investigated by carrying out the same operations as in Example 1. As the result, the class and subclass of PG11 were found to belong to IgG$_2$a. The human Mn-SOD activity of the supernatant obtained by the reaction of PG11 with protein A agarous solution was remarkably lowered (as shown in FIG. 1), because it is more readily reactive with protein A than NI8 and PE9. PG11 was recognized to have a high specific reactivity with human Mn-SOD, and no reactivity with other proteins.

EXAMPLE 4

Production of a Monoclonal Antibody Against Human Mn-SOD by Flask Cultivation

The cell culture of the NI8 cell line obtained by culturing in RPMI1640 medium containing 15% fetal bovine serum was transferred into 10 ml of RPMI1640 solution (containing no fetal bovine serum), and cultured to a state immediately before death.

The monoclonal antibody against human Mn-SOD (NI8) was found to be contained in the supernatant obtained by centrifugation of the culture broth (rotational number: 3000 rpm, time: 5 minutes) at a concentration of 35 μg/ml (measured by the single radial immunodiffusion method).

EXAMPLE 5

Production of a Monoclonal Antibody Against Human Mn-SOD Intraperitoneally in Mouse For obtaining a large amount of monoclonal antibody against human Mn-SOD, the cells of PG11 cell line were cultured intraperitoneally in mouse.

A suspension of 5×10$^6$ cells of PG11 cell line in RPMI1640 was administered intraperitoneally into a BALB/c mouse (female, 6 weeks old, administered intraperitoneally with 0.5 ml of pristane 2 weeks before).

The body weight of the mouse exhibited remarkable increase after about one week, and the ascites (10 ml/mouse) was collected on the second week. The ascites was centrifuged (rotational number: 3000 rpm, time: 5 minutes) to obtain ascites supernatant.

The monoclonal antibody against human Mn-SOD (PG11) was found to be contained in the ascites supernatant at a concentration of 8.0 mg/ml (measured by the single radial immunodiffusion method).

REFERENCE EXAMPLE 1

Production and Purification of Antibody

The PG11 cell line producing a monoclonal antibody having high specificity against human Mn-SOD (FERM-P No.1608) was cultured, and 10$^7$ of the cultured cells floated in phosphate buffer were administered intraperitoneally into a BALB/c mouse (male, 8 weeks old, administered intra-peritoneally with 0.5 ml of pristane 2 weeks before). The mouse body weight exhibited remarkable increase after about one week, and ascites was taken out appropriately on the first to third weeks. The antibody titer of the monoclonal antibody thus obtained was 10$^6$ to 10$^8$.

Purification of the monoclonal antibody from ascites obtained was carried out as described below.

The above ascites was dialyzed against a Tris-hydrochloride buffer (pH 7.4), and passed through a DEAE cellolose column equilibrated with the same buffer. The fractions passed as such were salted out with 50% saturated ammonium sulfate, and the precipitates obtained were dissolved in a phosphate buffer (pH 7.4), followed by dialysis against the same buffer. The purity of the monoclonal antibody against human Mn-SOD thus obtained was found to be high in all antibodies according to slab gel electrophoresis by use of SDS polyacrylamide gel.

According to the human Mn-SOD assay method (ELISA) by use of the purified monoclonal antibody against human Mn-SOD ("antibody") obtained as described above, it has become possible to assay human Mn-SOD at high sensitivity and also rapidly.

EXAMPLE 6

Preparation of "Enzyme-Labelled Antibody"

As the antibody in "enzyme-labelled antibody", the purified monoclonal antibody ("antibody") obtained in Reference example 1 was used.

By use of the monoclonal antibody, the antibody was labelled with an enzyme as described below to obtain the "enzyme-labelled antibody" in the assay kit in the present invention.

First, 8.5 mg of horseradish peroxidase was dissolved in 1 ml of distilled water, 200 μl of 0.1M sodium metaperiodate was added and the mixture was left to stand stationarily at room temperature for 30 minutes. The enzyme solution was dialyzed at 4° C. overnight by use of a 1 mM acetate buffer (pH 4.5), and then 100 μl of a 0.2M sodium carbonate buffer (pH 9.5) was added to adjust the pH to 9.5.

On the other hand, 8.5 mg of the monoclonal antibody (PG-11) dissolved in a 0.1M phosphate buffer (pH 7.4) (hereinafter abbreviated as PBS) was dialyzed at 4° C. overnight by use of a 0.01M sodium carbonate buffer (pH 9.5). The peroxidase and the monoclonal antibody thus obtained were mixed, left to stand stationarily at room temperature for 2 hours and half, and sodium tetrahydrideborate was added to the reaction mixture, followed by leaving to stand stationarily at 4° C. for 2 hours. The perioxidase-conjugated monoclonal antibody thus obtained was dialyzed at 4° C. overnight by use of PBS, and added each in 10 μl into a vial to provide "enzyme-labelled antibody" (30 μg/vial) which is the assay kit of human Mn-SOD. During assay of human Mn-SOD, it was appropriately diluted with PBS before use.

EXAMPLE 7

Figure 2:
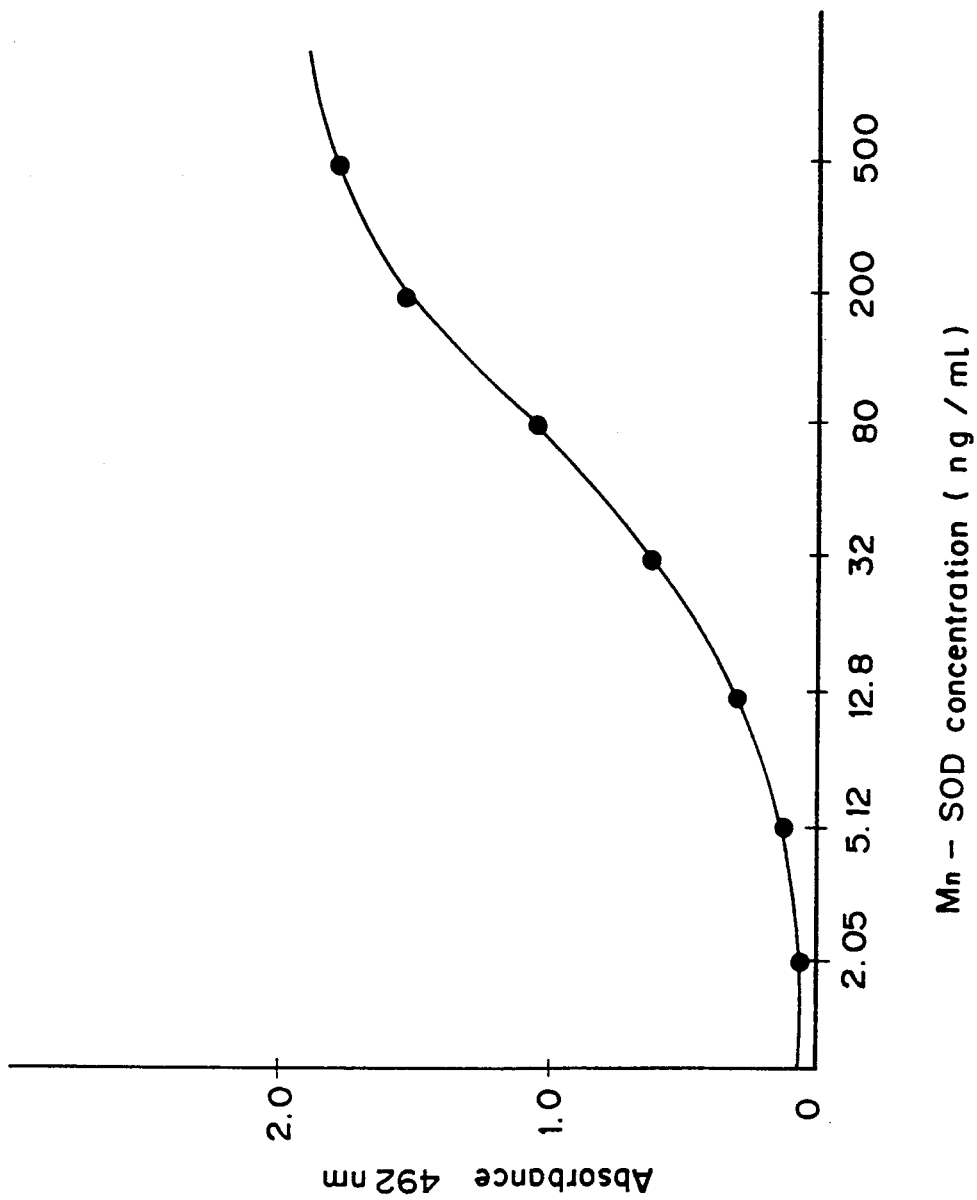
FIG. 2 shows the standard curve of human Mn-SOD prepared according to the stepwise reaction method in the assay method of human Mn-SOD of the present invention.

Preparation of Calibration Curve According to the Stepwise Reaction Method of Human Mn-SOD by Use of Assay Kit of Human Mn-SOD The "antibody" solution of Reference example 1 (10 μg/ml, dissolved with PBS) was added each in 100 μl in a 96-well flat-bottomed plate for immunoassay which is the carrier (polystyrene microplate of Nunc Company), followed by leaving to stand stationarily under 4° C. overnight to have the "antibody" immobilized on each well. Next, for removing the "antibody" not immobilized on the carrier, each well was washed with a washing solution comprising PBS containing 0.05% Tween 20. Further, for preventing non-specific adsorption of human Mn-SOD or "enzyme-labelled antibody" onto the plate, each 200 μl of PBS containing 0.1% BSA was added into each well, followed by leaving to stand stationarily at room temperature for 30 minutes. Next, after washing with the same washing solution, "standard human Mn-SOD solution" (2, 5, 13, 32, 80, 200, 500 ng/ml, dissolved with PBS) was prepared, and each 100 μl was added into each well, followed by leaving to stand stationarily at room temperature for one hour. Next, after washing with the same washing solution, each 100 μl of the "enzyme-labelled antibody" solution obtained in Example 6 was added into each well, followed by leaving to stand stationarily at room temperature for one hour. Next, after washing with the same washing solution, each 100 μl of "substrate solution" (10 mg of o-phenylenediamine and 5 μl of 35% $H_2O_2$ dissolved in 25 ml of 0.1M citrate buffer) was added into each well, followed by leaving to stand under the state shielded from light at room temperature for 15 minutes. Finally, further each 50 μl of 2 N sulfuric acid was added to stop the enzymatic reaction, and absorbance of the solution at 492 nm after stopping of the reaction was measured by use of a microplate spectrophotometer. As the result, an assay of human Mn-SOD according to the stepwise reaction method by use of "enzyme-labelled antibody" could determine human Mn-SOD at high sensitivity within about 2 hours and half by use of the 96-well flat-bottomed plate for immunoassay (polystyrene microplate of Nunc Company) having "antibody" fixed thereon. The results are shown in FIG. 2.

EXAMPLES 8-10

Dilution Test of Serum According to the Stepwise Reaction Method

Figure 3:
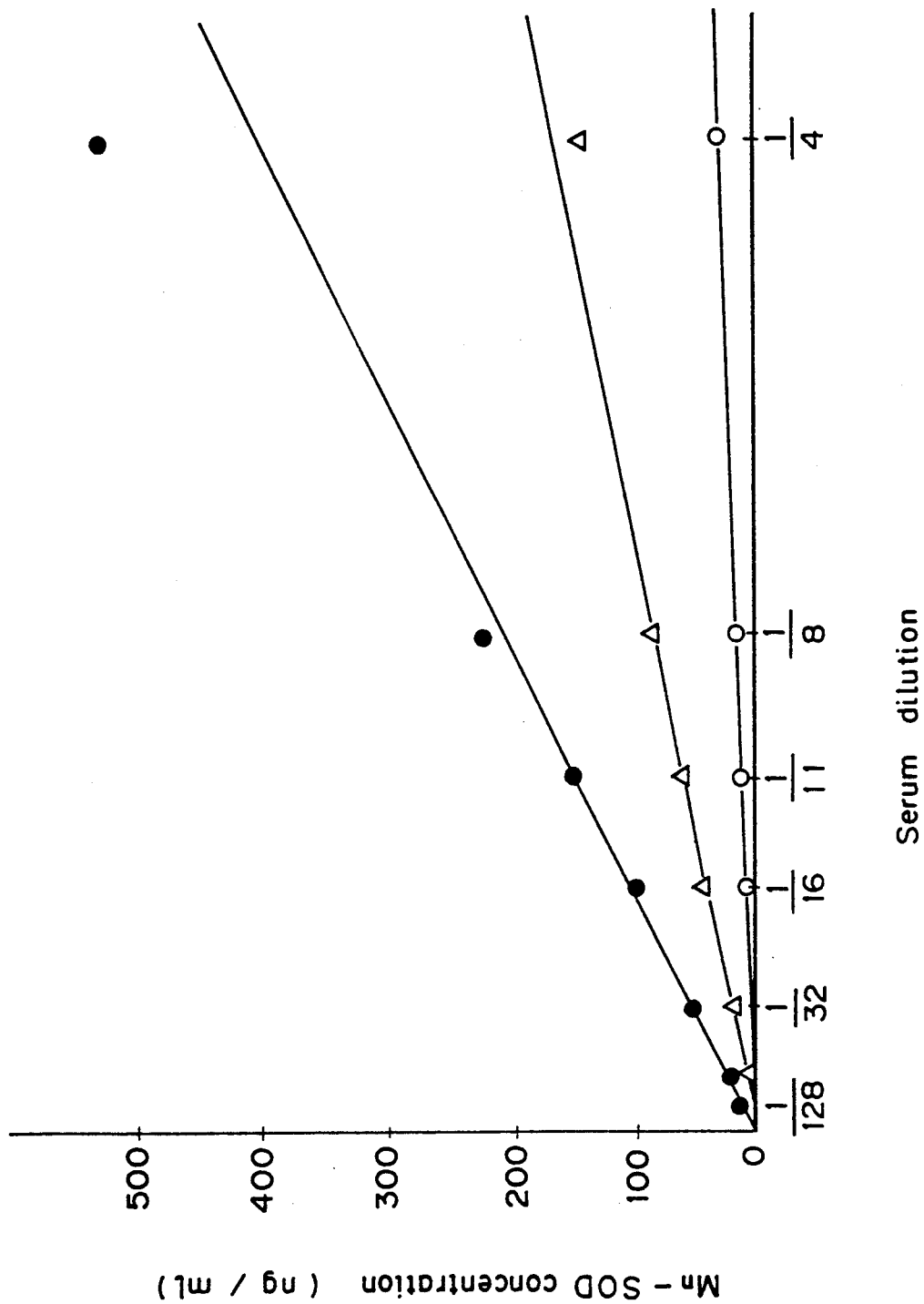
FIG. 3 shows the dilution test with the standard serum determined according to the stepwise reaction method in the assay method of human Mn-SOD of the present invention.

Human Mn-SOD was assayed in the same manner as in Example 7 except for using solutions obtained by diluting to 4-fold, 8-fold, 16-fold, 32-fold, 64-fold, 128-fold a solution of human Mn-SOD prepared by diluting it to a concentration of 220, 660 or 1800 ng/ml with human standard serum (Nescol X manufactured by Kaketsuken) in place of the "standard human Mn-SOD solution" in Example 7. As the result, dilution linearity was recognized within the dilution range from 8 to 128-fold. The results are shown in FIG. 3.

EXAMPLES 11-12

Addition and Recovery Test of Human Mn-SOD According to the Stepwise Reaction Method Human Mn-SOD was assayed in the same manner as in Example 7 except for using a solution prepared by diluting with a diluent (0, 50, 100 ng/ml; dissolved in Nescol X solution manufactured by Kaketsuken) containing human Mn-SOD to 11-fold in place of the "standard human Mn-SOD solution" in Example 7. As the result, the amount of human Mn-SOD added substantially coincided with the amount of human Mn-SOD actually determined. The results are shown in Table 1.

TABLE 1

| Example | Amount added (ng/ml) | Measured value (ng/ml) | Amount recovered (ng/ml) | Recovery (%) |
| --- | --- | --- | --- | --- |
|    | 0  | 67.1  | —    | —     |
| 11 | 50 | 119.9 | 52.8 | 105.6 |

TABLE 1-continued

| Example | Amount added (ng/ml) | Measured value (ng/ml) | Amount recovered (ng/ml) | Recovery (%) |
| --- | --- | --- | --- | --- |
| 12 | 100 | 161.7 | 94.6 | 94.6 |

EXAMPLE 13

Figure 4:
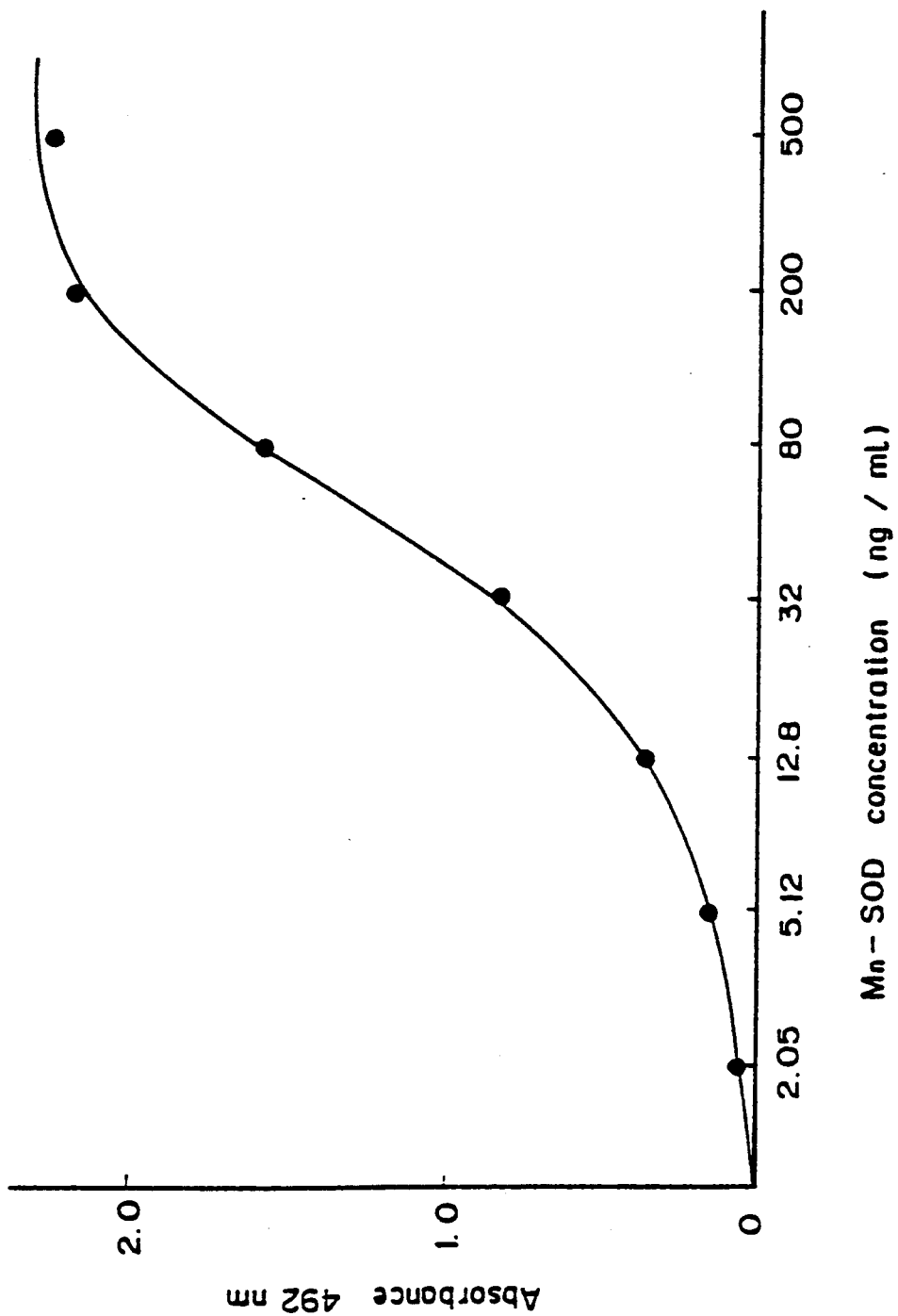
FIG. 4 shows the standard curve of human Mn-SOD prepared according to the mixed solution reaction method in the assay method of human Mn-SOD of the present invention.

Preparation of a Calibration Curve According to the Mixed Solution Reaction Method of Human Mn-SOD by Use of Assay Kit of Human Mn-SOD The "antibody" solution of Reference example 1 (10 μg/ml, dissolved with PBS) in Reference example 1 was added each in 100 μl into a 96-well flat-bottomed plate for immunoassay (polystyrene microplate of Nunc Company), followed by leaving to stand stationarily at 4° C. overnight to have "antibody" immobilized on each well. Next, for removing the "antibody" not immobilized on the carrier, each well was washed with a washing solution comprising PBS containing 0.05% Tween 20. Further, for preventing non-specific adsorption of human Mn-SOD or "enzyme-labelled antibody" onto the plate, each 200 μl of PBS containing 0.1% BSA was added into each well, followed by leaving to stand stationarily at room temperature for 30 minutes. Next, after washing with the same washing solution, a mixture comprising a known amount of human Mn-SOD solution and the "enzyme-labelled antibody" of Example 1 was prepared as "standard human Mn-SOD solution" (2, 5, 13, 32, 80, 200, 500 ng/ml, dissolved with PBS), and each 100 μl was added into each well, followed by leaving to stand stationarily at room temperature for one hour. Next, after washing with the same washing solution, each 100 μl of "substrate solution" (10 mg of o-phenylene-diamine and 5 μl of 35% $H_2O_2$ dissolved in 25 ml of 0.1M citrate buffer) was added into each well, followed by leaving to stand under the state shielded from light at room temperature for 15 minutes. Finally, further each 50 μl of 2N sulfuric acid was added to stop the enzymatic reaction, and absorbance of the solution at 492 nm after stopping of the reaction was measured by use of a microplate spectrophotometer. As the result, assay of human Mn-SOD according to the mixed solution reaction method by use of "enzyme-labelled antibody" could determine human Mn-SOD at high sensitivity within about one hour and half by use of the 96-well flat-bottomed plate (polystyrene microplate of Nunc Company) having "antibody" fixed thereon. The results are shown in FIG. 4.

EXAMPLES 14-15

Addition and Recovery Test of Human Mn-SOD According to the Mixed Solution Reaction Method Human Mn-SOD was assayed in the same manner as in Example 13 except for using a solution prepared by diluting with a diluent (0, 100, 250 ng/ml; dissolved in Nescol X solution manufactured by Kaketsuken) containing human Mn-SOD to 11-fold in place of the "standard human Mn-SOD solution" in Example 13. As the result, the amount of human Mn-SOD added substantially coincided with the amount of human Mn-SOD actually determined. The results are shown in Table 2.

TABLE 2

| Example No. | Amount added (ng/ml) | Measured value (ng/ml) | Amount recovered (ng/ml) | Recovery (%) |
|---|---|---|---|---|
|  | 0 | 92.4 | — | — |
| 14 | 100 | 189.2 | 96.8 | 96.8 |
| 15 | 250 | 319.0 | 226.6 | 90.6 |

COMPARATIVE EXAMPLES 1-5

Figure 5:
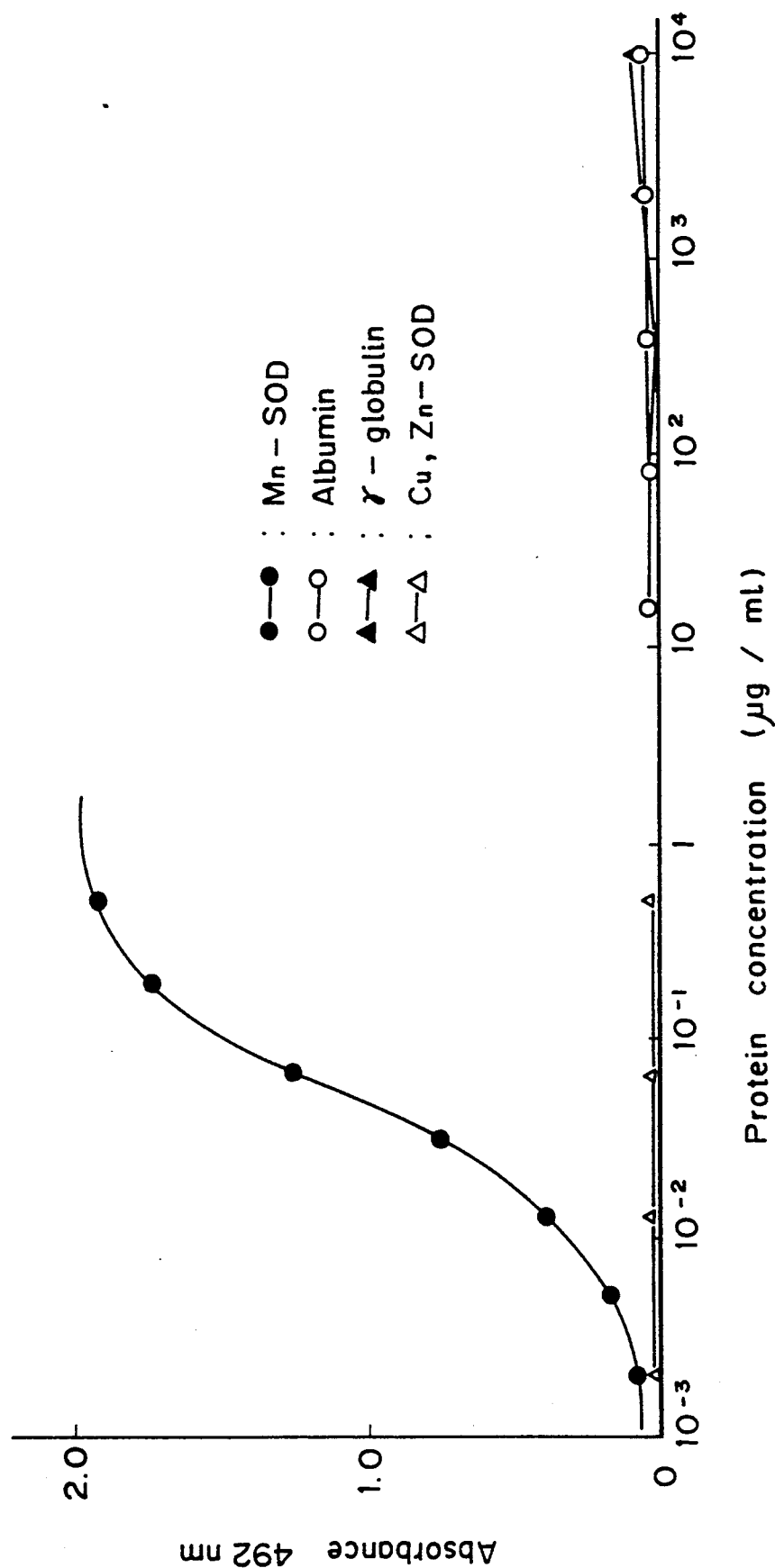
FIG. 5 shows the results of investigation of cross-reactivities with albumin, $\alpha$-globulin, $\beta$-globulin, $\gamma$-globulin, hemoglobin, Cu, Zn-superoxide dimustase which are human serum proteins according to the stepwise reaction method.

Crossreactivities with Human Serum Proteins According to the Stepwise Reaction Method In the same manner as in Example 7 except for using solutions of albumin, α-globulin, β-globulin, γ-globulin, hemoglobin, Cu, Zn-superoxide dismutase which are human serum proteins in place of the "standard human Mn-SOD solution" in Example 7, crossreactivities with those human serum proteins were investigated. As the result, substantially no absorbance at 492 nm was observed in all the human serum proteins (namely, all the human serum proteins did not interfere with the present assay; since both α-globulin and β-globulin did not react at all, their graphs were omitted). The results are shown in FIG. 5.

COMPARATIVE EXAMPLES 6-10

Figure 6:
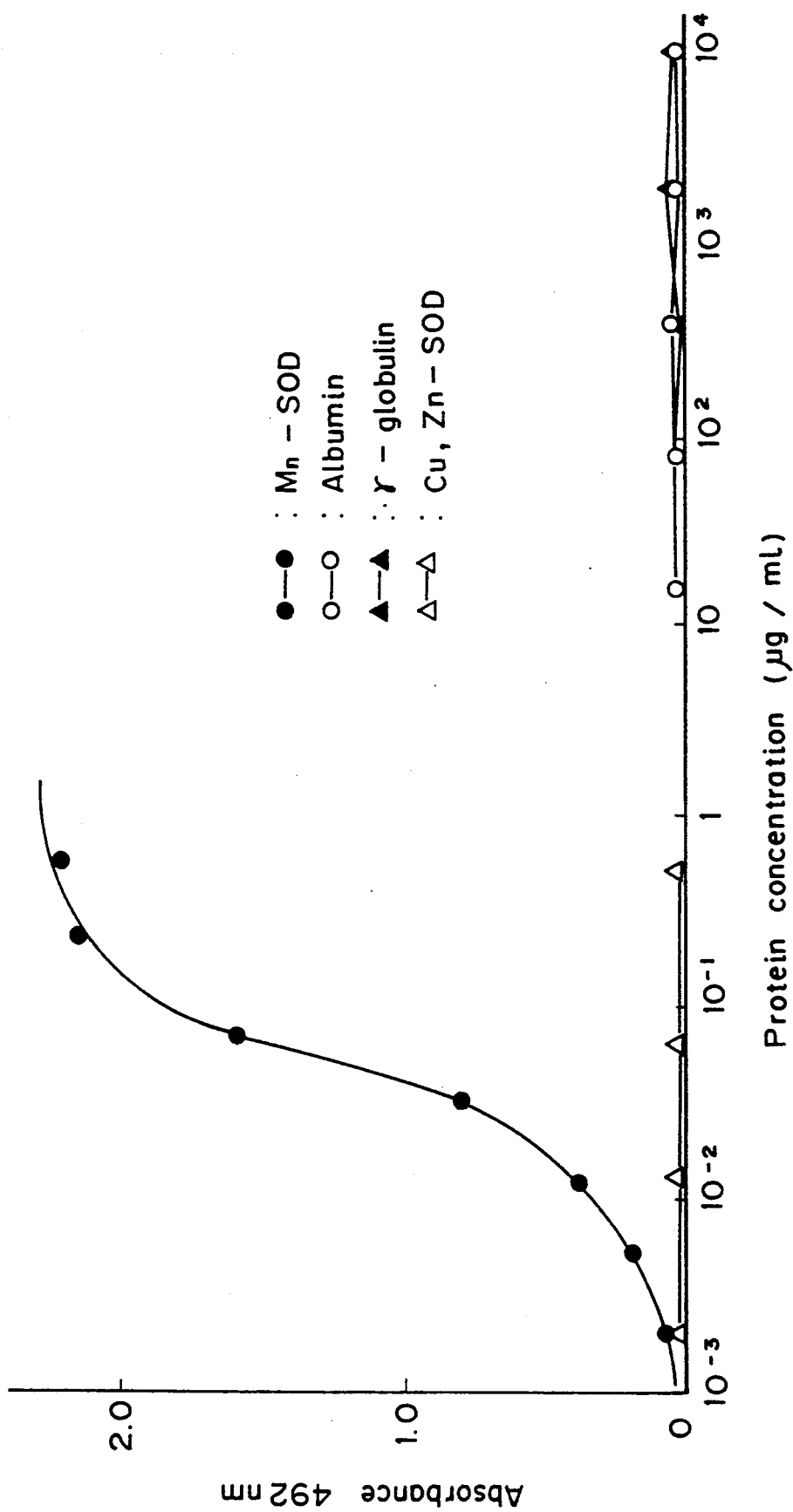
FIG. 6 shows the results of investigation of cross-reactivities with albumin, $\alpha$-globulin, $\beta$-globulin, $\gamma$-globulin, hemoglobin, Cu, Zn-superoxide dimustase which are human serum proteins according to the mixed solution reaction method.

Crossreactivities with Human Serum Proteins According to the Mixed Solution Reaction Method In the same manner as in Example 13 except for using solutions of albumin, α-globulin, β-globulin, γ-globulin, hemoglobin, Cu, Zn-superoxide dismutase which are human serum proteins in place of the "standard human Mn-SOD solution" in Example 13, crossreactivities with those human serum proteins were investigated. As the result, substantially no absorbance at 492 nm was observed in all the human serum proteins (namely, all the human serum proteins did not interfere with the present assay; since both α-globulin and β-globulin did not react at all, their graphs were omitted). The results are shown in FIG. 6.

EXAMPLES 16-25

Assay of Human Mn-SOD Concentration in Various Female Patients Sera

In the assay method of human Mn-SOD in Example 7, in place of the "standard human Mn-SOD solution", using sera diluted with a diluent to 10-fold of various disease patients as shown in Table 3 [epithelial ovarian cancer (Example 16: 23 cases), non-epithelial ovarian cancer (Example 17: 12 cases), endometrial cancer of the uterus (Example 18: 15 cases), cervical cancer of the uterus (Example 19: 7 cases), lung cancer (Example 20: 4 cases), hepatoma (Example 21: 7 cases), melanoma (Example 22: 3 cases), other cancer diseases in the fields of gynecotokology (including choriocarcinoma, vulvar cancer, breast cancer; Example 23: 8 cases), liver cirrhosis (Example 24: 8 cases), other diseases in the fields of obsterics and gynecology (endometriosis, ovarian cyst, villous diseases, partial mole; Example 25: 7 cases), those human Mn-SOD concentrations were assayed. As Control, sera of healthy women (Control: 207 cases) diluted with a diluent to 10-fold were used in place of female patients sera. The results are shown in Table 3.

TABLE 3

|  | Mn-SOD concentration (ng/ml) | | | | Average value of concentration | Number of case | Positive ratio (%) |
|---|---|---|---|---|---|---|---|
|  | 130 or lower | 131-200 | 201-300 | 301 or more |  |  |  |
| Example 16 | 12 cases | 3 cases | 4 cases | 4 cases | 183 | 23 | 48 |
| Example 17 | 12 |  |  |  | 90 | 12 | 0 |
| Example 18 | 14 | 1 |  |  | 92 | 15 | 7 |
| Example 19 | 6 | 1 |  |  | 109 | 7 | 14 |
| Example 20 | 3 | 1 |  |  | 120 | 4 | 25 |
| Example 21 | 5 | 1 | 1 |  | 125 | 7 | 29 |
| Example 22 | 3 |  |  |  | 89 | 3 | 0 |
| Example 23 | 7 | 1 |  |  | 97 | 8 | 13 |
| Example 24 | 5 | 3 |  |  | 113 | 8 | 38 |
| Example 25 | 7 |  |  |  | 94 | 7 | 0 |
| Control | 109 | 10 |  |  | 89 ± 21 | 207 | 5 |

EXAMPLE 26

Monitoring of Prognosis of Epithelial Ovarian Cancer Patient by Assay of Human Mn-SOD Concentration Monitoring of prognosis was carried out by monitoring the therapeutical course after operation of 23 cases of epithelial ovarian cancer patients by assaying the human Mn-SOD concentration in serum with lapse of time.

More specifically, in the assay method of human Mn-SOD in Example 7, by use of the serum which has been blood with lapse of time from the epithelial ovarian cancer patient and diluted with a diluent to 10-fold in place of the "standard human Mn-SOD solution", the human Mn-SOD concentration in the serum of each patient was assayed.

Figure 7:
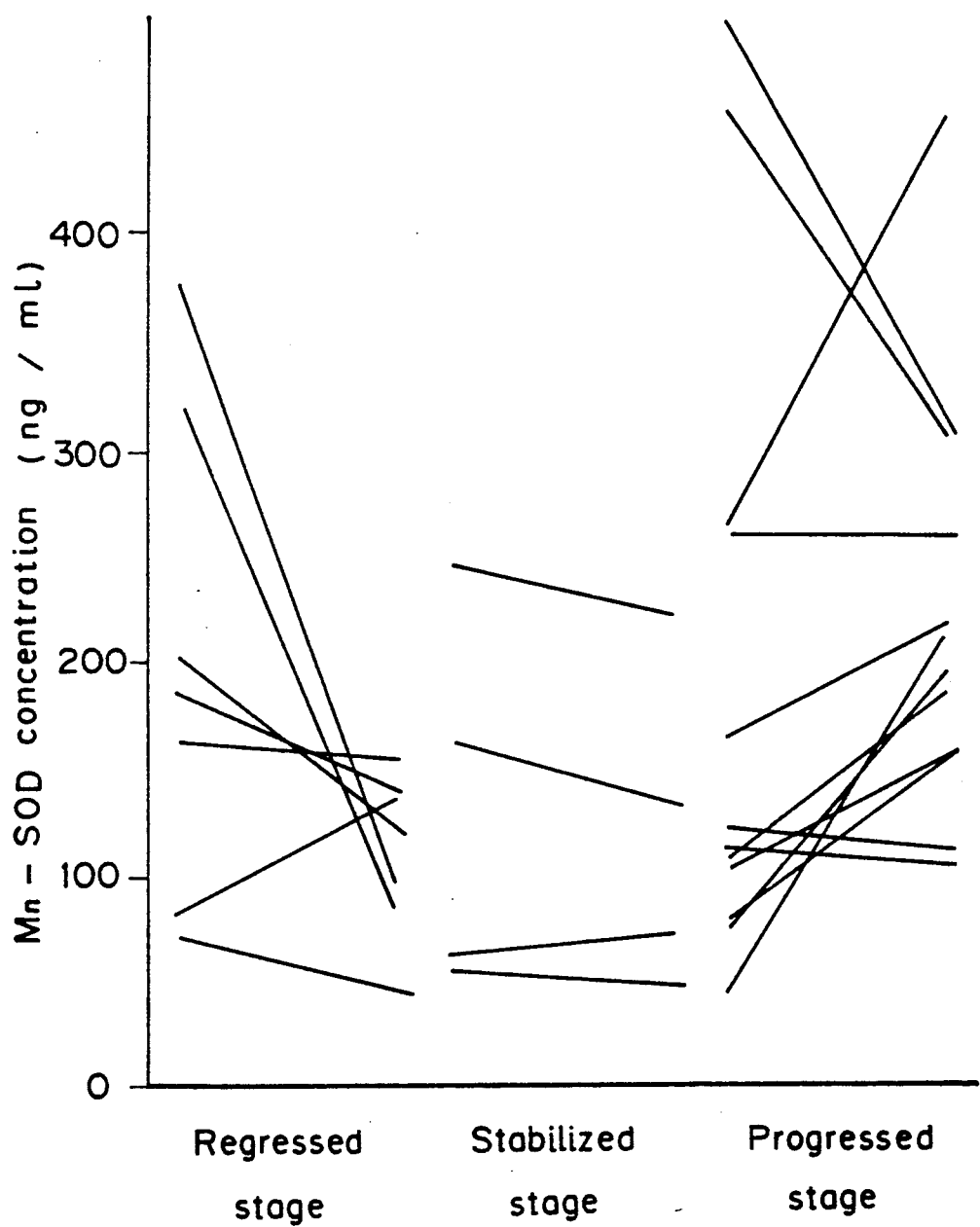
FIG. 7 shows the fluctuations in human Mn-SOD concentration in the respective sera of 23 cases during regressed stage, stabilized stage and progressed stage after operation of epithelial ovarian cancer patients.
Figure 8:
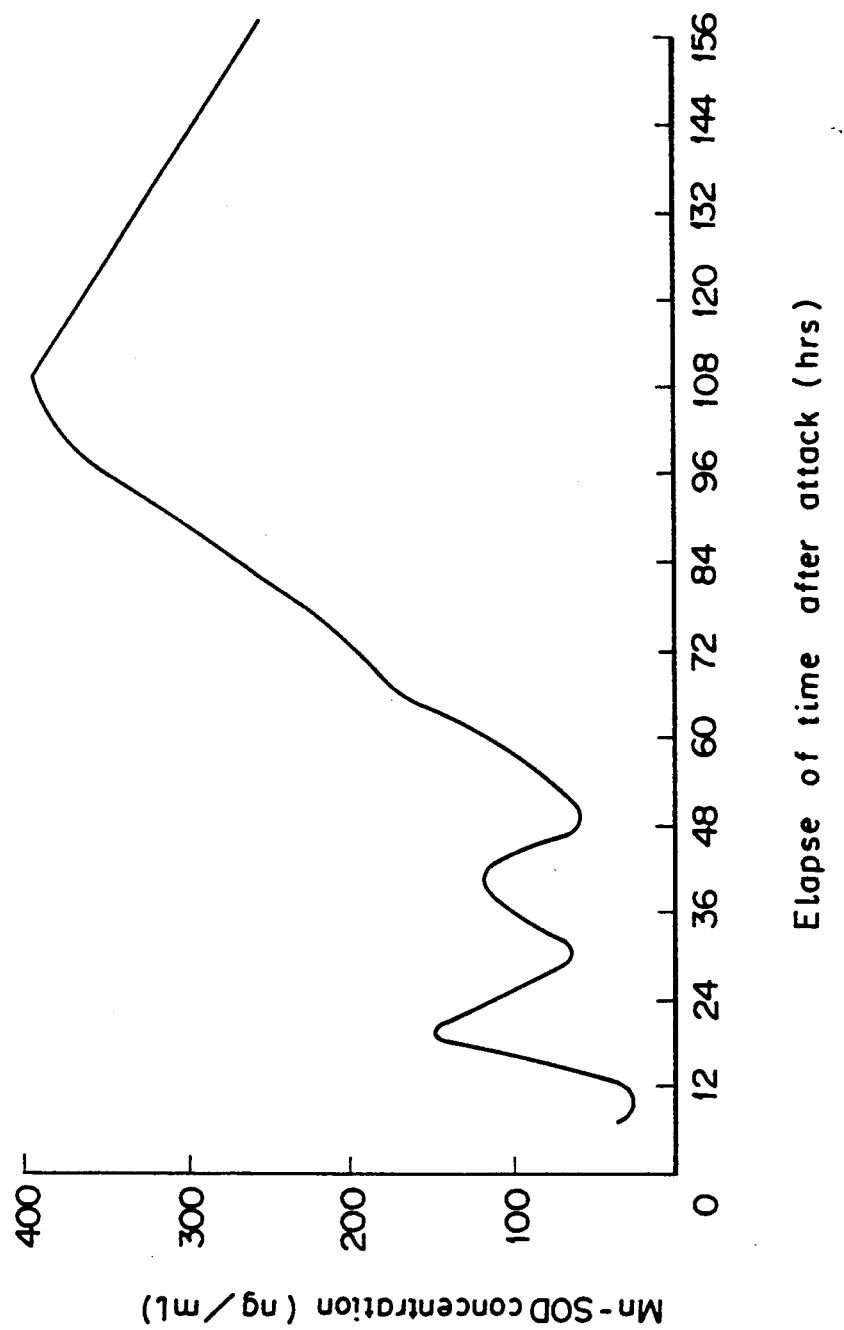
FIGS. 8 to 14 illustrate fluctuations in human Mn-SOD concentration in respective sera from 7 cases of myocardial infarction patients with drawing blood when the stroke time being as the hour 0 in the novel diagnostic method of myocardial infarction of the present invention.
Figure 9:
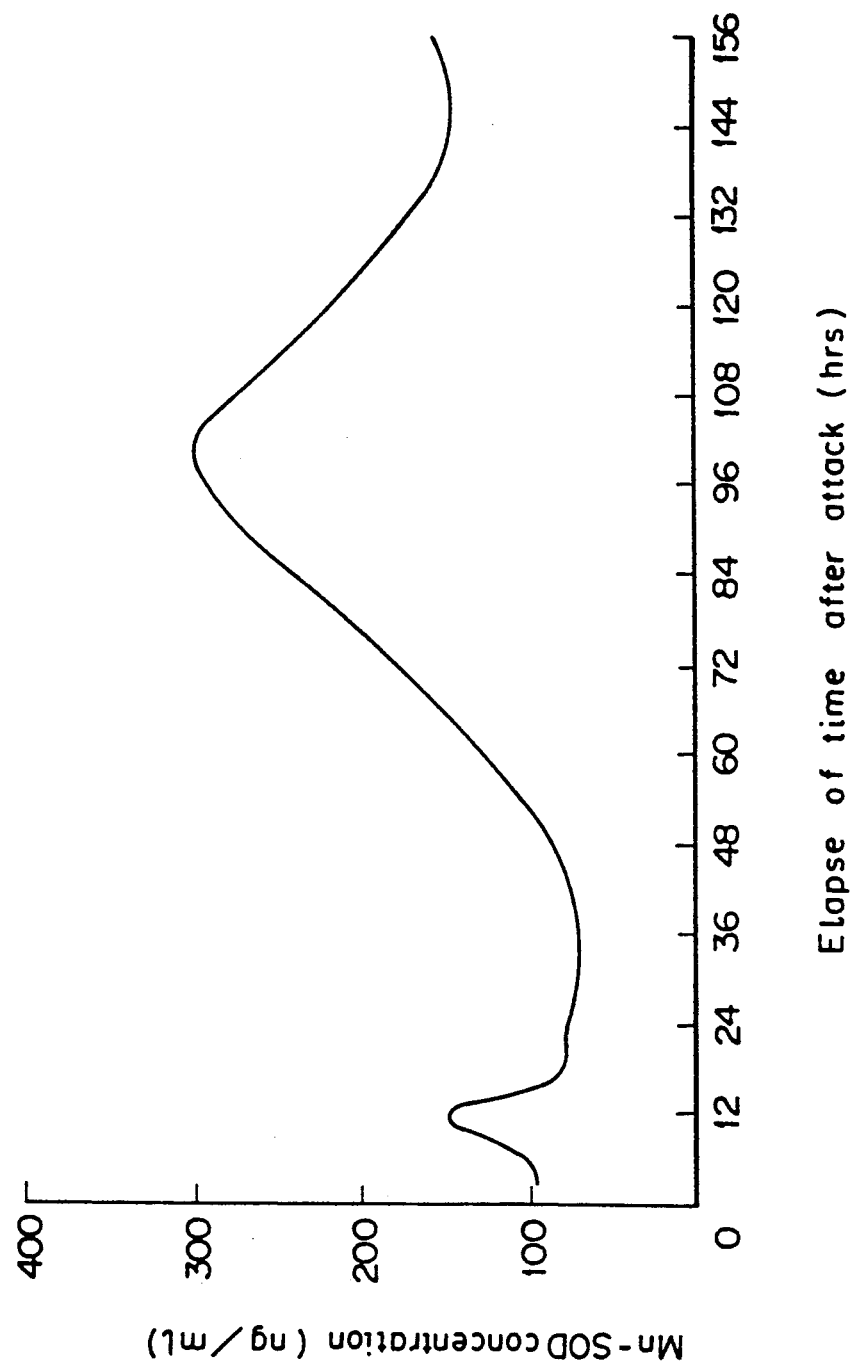
Figure 10:
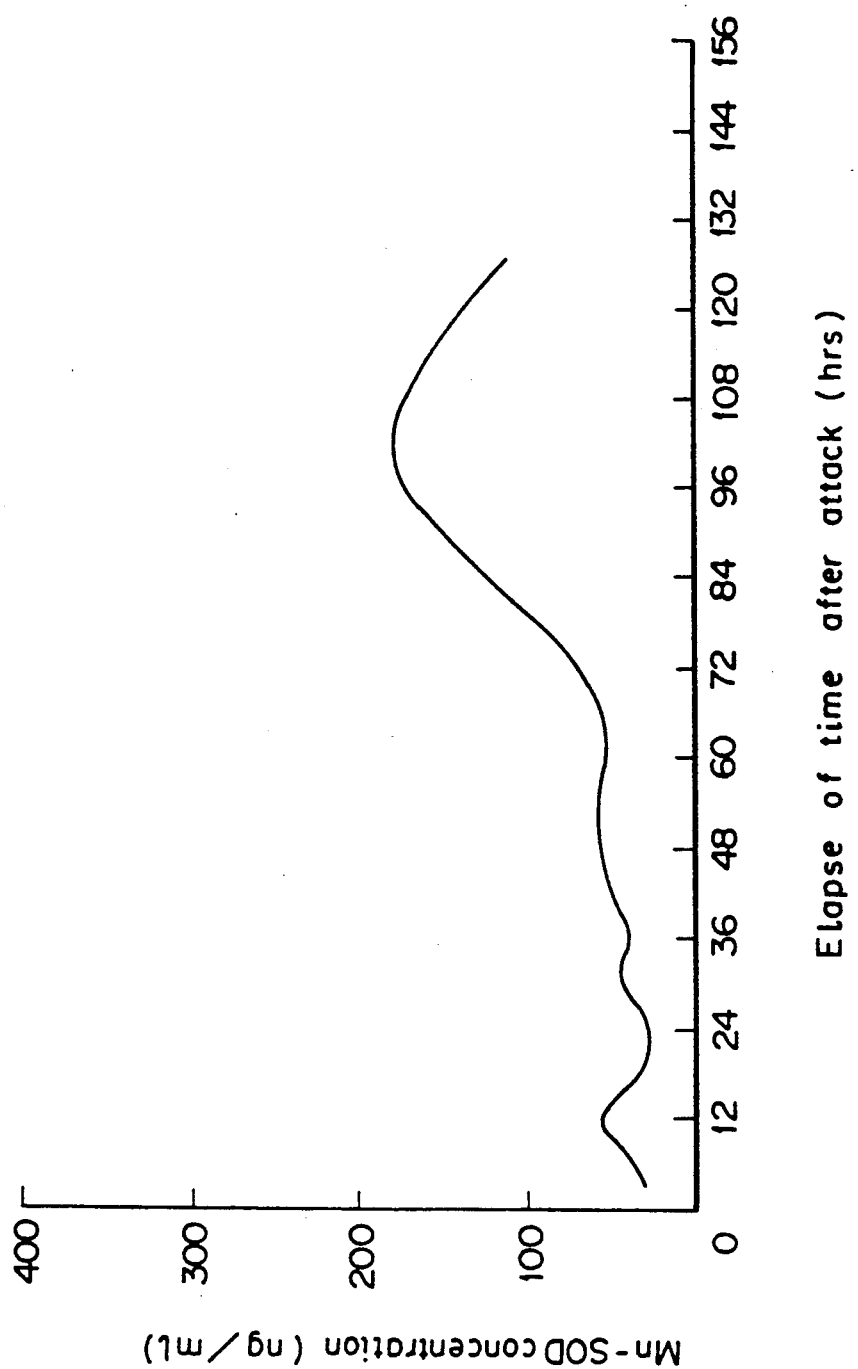
Figure 11:
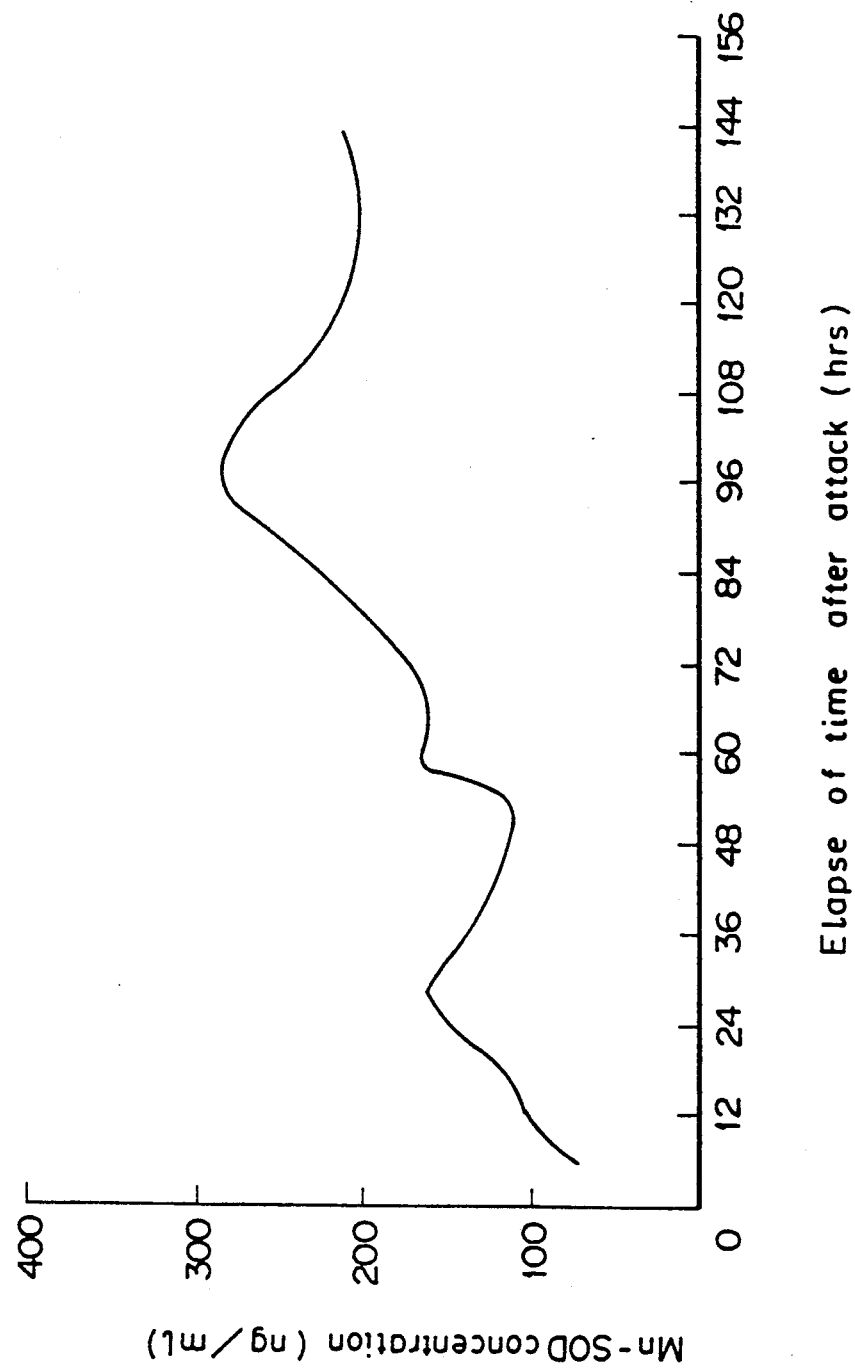
Figure 12:
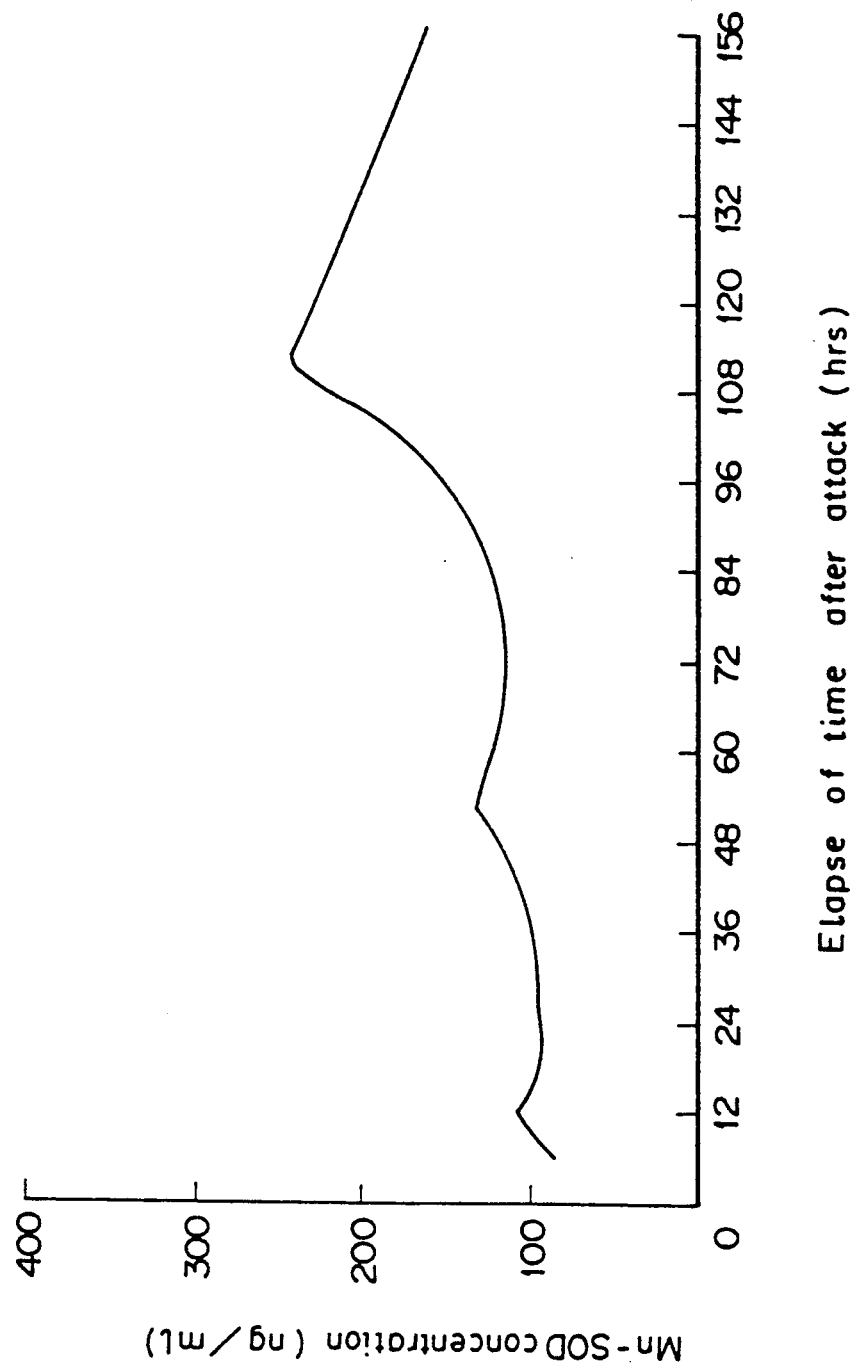
Figure 13:
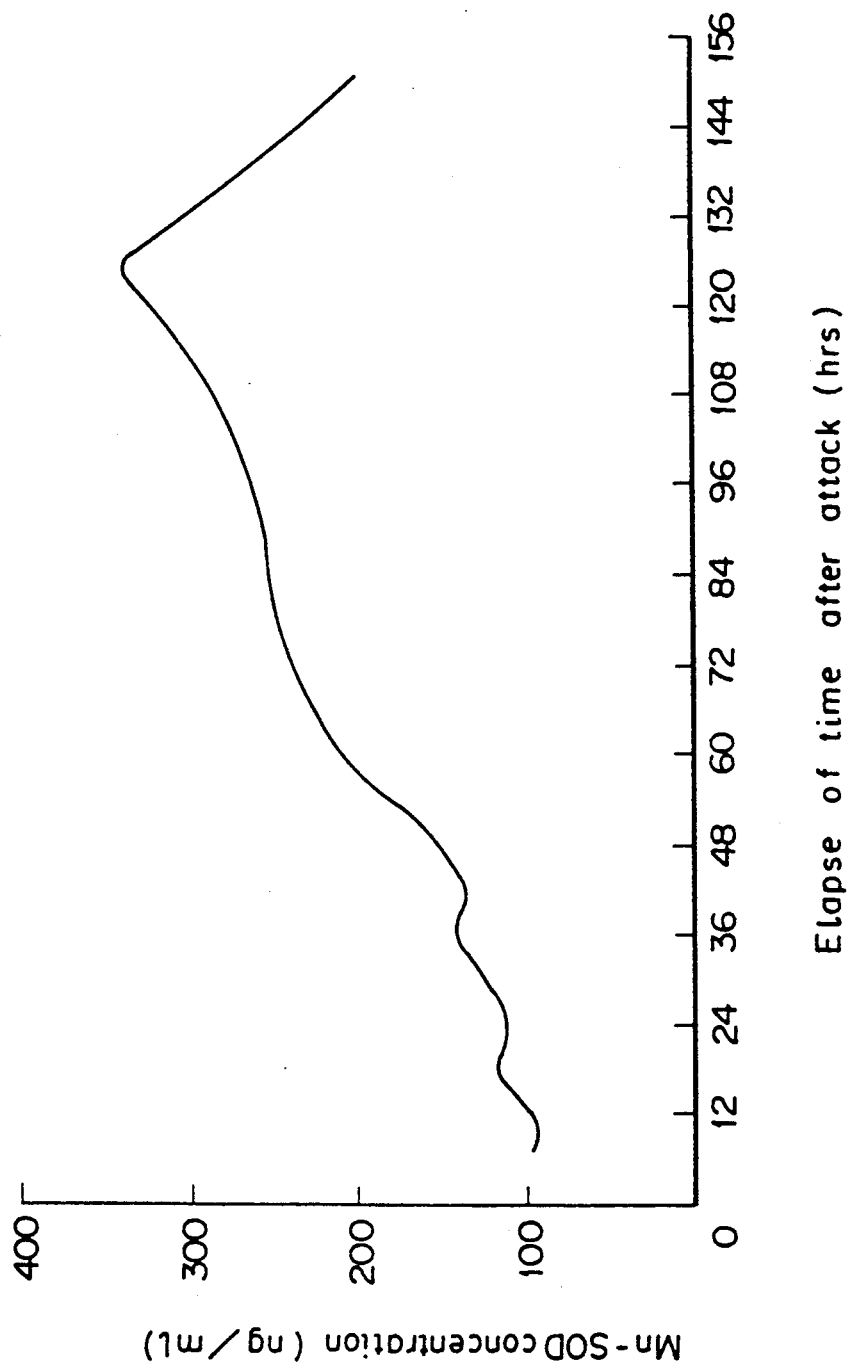
Figure 14:
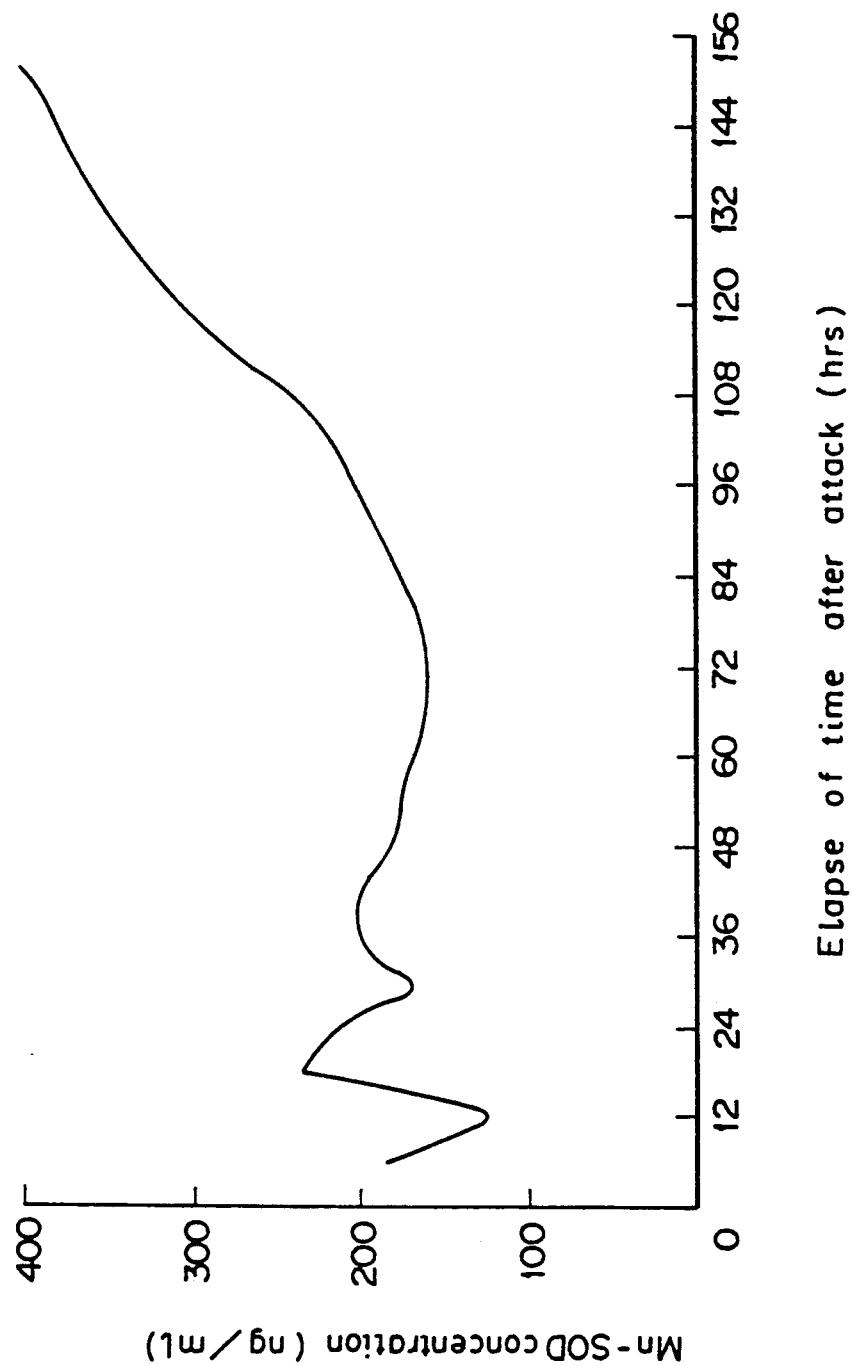

Of the above 23 cases, 7 cases exhibited regressed stage, 4 cases stabilized stage and 12 cases progressed stage. The relationship between those therapeutical courses and human 20Mn-SOD concentration is shown in Table 4 and FIG. 7.

TABLE 4

| Mn-SOD concentration | Regressed stage | Stabilized stage | Progressed stage |
|---|---|---|---|
| Decreased | 6 cases | 1 case | — |
| Constant | 1 case | 3 cases | 4 cases |
| Increased | — | — | 8 cases |

EXAMPLE 27

Assay of Mn-SOD Concentration in the Serum of Myocardial Infarction Patient

In the assay method of human Mn-SOD concentration in Example 7, by use of 7 cases of sera of myocardial infarction patients drawed blood with lapse of time diluted to 11-fold in place of the "standard human Mn-SOD solution", human Mn-SOD concentrations in those were assayed. The results of assay with lapse of time of Mn-SOD concentrations in the sera of respective patients are shown in FIGS. 8 to 14.

In all of the 7 cases (FIGS. 8 to 14) the first peak was recognized after 12 to 24 hours after stroke in biological indexes of CPK, GOT, and the first peak was recognized after 30 to 60 hours after a stroke in biological index of LDH, but the first peak was recognized after 10 to 24 hours after a stroke in biological index of Mn-SOD.

In 6 cases (FIGS. 8-13), "diagnosis stage" (the term wherein a high value state of 150 ng/ml of the Mn-SOD concentration is persistent within the period of about 110±10 hours or longer) is recognized.

In one case (FIG. 14), the Mn-SOD concentration continued to be increased even after a lapse of about 110 hours after a stroke, until it exhibited a high value state of 400 ng/ml or higher, and the patient was dead without the therapeutical effect being recognized.

CPK concentration was assayed by use of a serum immediately after drawing blood on the basis of the UV-ray portion method (Genji Kitamura, Shiro Miwa et al, eds.; Clinical Test Manual, p. 197, Bunkodo, 1988).

Amelioration ratio (%) of heart function according to left venticulography contrast was determined by determining chronic stage ejection fraction, acute stage ejection fraction on the basis of contrast diagnosis (Genji Kitamura, Shiro Miwa et al, eds.; Clinical Test Manual, p. 1110, Bunkodo, 1988) and calculating according to the following formula:

$$\text{Amelioration ratio} = \frac{\text{Chronic stage ejection fraction} - \text{Acute stage ejection fraction}}{\text{Acute stage ejection fraction}} \times 100$$

EXAMPLE 28

Relationship Between the Maximum Value of Mn-SOD Concentration and the Maximum Value of CPK Concentration in "Diagnosis Stage"

Figure 15:
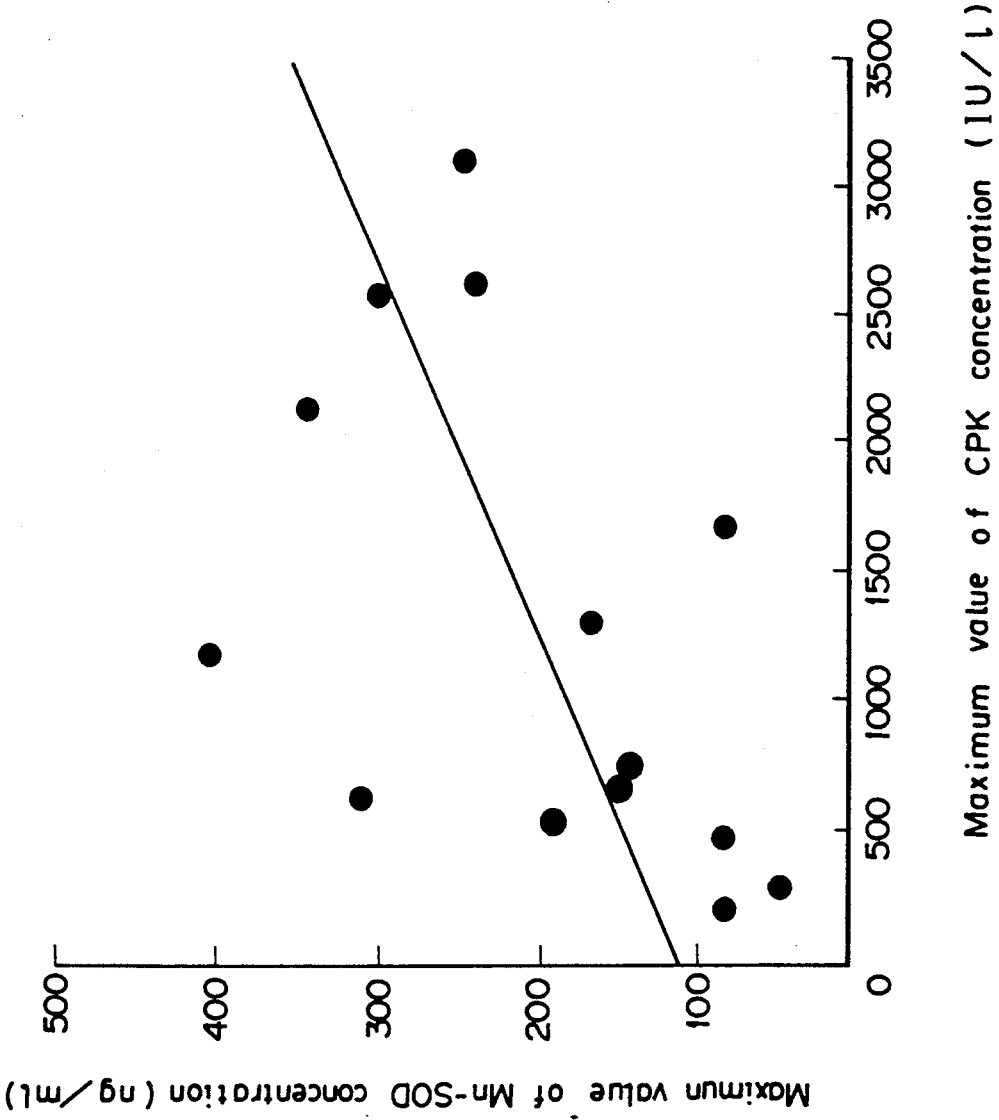
FIG. 15 shows the relationship between the maximum value of Mn-SOD concentration at a "diagnosis stage" and the maximum value of CPK concentration in each serum of 15 cases of myocardial infarction patients.

In the assaying method of human Mn-SOD in Example 7, by use of a part of sera of 15 cases of myocardial infarction patients which has been drawed blood with lapse of time and diluted to 11-fold in place of the "standard human Mn-SOD solution", human Mn-SOD concentrations in those were assayed. Also, by use of the same sera, concentrations of CPK were assayed to determine the relationship between the maximum value of Mn-SOD concentration and the maximum value of CPK concentration in "diagnosis stage". The results are shown in FIG. 15.

EXAMPLE 29

Relationship Between the Maximum Value of Mn-SOD Concentration and Amelioration Ratio of Heart Function in "Diagnosis Stage"

In the assay method of human Mn-SOD in Example 7, by use of sera of 14 cases of myocardial infarction patients which has been drawed blood with lapse of time and diluted to 11-fold in place of the "standard human Mn-SOD solution", human Mn-SOD concentrations in those were assayed. From the maximum value of the Mn-SOD concentration in "diagnosis stage" thus determined and the amelioration ratio of heart function measured by left ventricular contrast, relationship between the both was determined. The results are shown in FIG. 16.

The "monoclonal antibody having a very high specific reactivity against human Mn-SOD obtained by culturing of a cell line" of the present invention can be expected to have uses for reagents for basic researches concerning human Mn-SOD, and assay reagents to be used in clinical tests, and by use of an assay reagent or assay kit of human Mn-SOD comprising essentially "antibody", "enzyme-labelled antibody", human Mn-SOD can be assayed easily, rapidly and at high sensitivity.

Further, according to the novel diagnostic method of ovarian cancer according to the present invention, by assaying human Mn-SOD concentration, it is possible to judge easily whether a patient is afflicted with epithelial ovarian cancer or not at considerably high probability, and it is also effective for monitoring of its prognosis, and further according to the novel diagnosis method of myocardial infarction of the present invention, by assaying human Mn-SOD concentration, diagnosis is possible easily without being affected by reperfusion performed after therapy of myocardial infarction, and also without carrying out frequent blood sampling.

I claim:

1. A method of screening for human epithelial ovarian cancer, which comprises (a) assaying for a concentration of human Mn-SOD in a body fluid by contacting the bodily fluid with a monoclonal antibody having a high specificity against human Mn-SOD, said monoclonal antibody not being reactive with any human albumin, human globulin, Cu and Zn-SOD, said monoclonal antibody being immobilized on a carrier, and (b) determining whether a concentration of 130 ng/ml or more of human Mn-SOD in a bodily fluid is present as an indication of the presence of epithelial ovarian cancer.

2. The method according to claim 1, wherein the monoclonal antibody is secreted from a hybridoma selected from the group consisting of FERM-BP 1606, FERM-BP 1607 and FERM-BP 1608.

3. A method of screening for myocardial infarction, which comprises (a) assaying for a concentration of human Mn-SOD in a body fluid by contacting the bodily fluid with a monoclonal antibody having a high specificity against human Mn-SOD, said monoclonal antibody not being reactive with any of human albumin, human globulin. Cu and Zn-SOD, said monoclonal antibody being immobilized on a carrier, and (b) determining whether a concentration of 150 ng/ml of more of human Mn-SOD in a bodily fluid is present as an indication of an occurrence of a myocardial infarction.

4. The method according to claim 3, wherein the monoclonal antibody is secreted from a hybridoma selected from the group consisting of FERM-BP 1606, FERM-BP 1607 and FERM-BP 1608.

* * * * *